(12) United States Patent
Cheng et al.

(10) Patent No.: US 7,172,896 B2
(45) Date of Patent: *Feb. 6, 2007

(54) INTEGRATED PORTABLE BIOLOGICAL DETECTION SYSTEM

(75) Inventors: Jing Cheng, Bejing (CN); Lei Wu, San Diego, CA (US); Michael J. Heller, Encinitas, CA (US); Ed Sheldon, Arcadia, CA (US); Jonathan Diver, San Diego, CA (US); James P. O'Connell, Solana Beach, CA (US); Dan Smolko, Jamul, CA (US); Shila Jalali, San Diego, CA (US); David Willoughby, San Diego, CA (US)

(73) Assignee: Nanogen, Inc., San Diego, CA (US)

( * ) Notice: Subject to any disclaimer, the term of this patent is extended or adjusted under 35 U.S.C. 154(b) by 460 days.

This patent is subject to a terminal disclaimer.

(21) Appl. No.: 10/163,835

(22) Filed: Jun. 5, 2002

(65) Prior Publication Data

US 2002/0155586 A1  Oct. 24, 2002

Related U.S. Application Data

(63) Continuation of application No. 09/470,448, filed on Dec. 22, 1999, now Pat. No. 6,403,367, and a continuation-in-part of application No. 09/016,596, filed on Jan. 30, 1998, now Pat. No. 6,071,394, and a continuation-in-part of application No. 08/986,065, filed on Dec. 5, 1997, now Pat. No. 6,051,380, which is a continuation-in-part of application No. 08/709,358, filed on Sep. 6, 1996, now Pat. No. 6,129,828, which is a continuation-in-part of application No. 08/534,454, filed on Sep. 27, 1995, now Pat. No. 5,849,486, which is a continuation-in-part of application No. 08/304,657, filed on Sep. 9, 1994, now Pat. No. 5,632,957, which is a continuation-in-part of application No. 08/271,882, filed on Jul. 7, 1994, now Pat. No. 6,017,696.

(60) Provisional application No. 60/113,730, filed on Dec. 23, 1998.

(51) Int. Cl.
*C12M 3/00* (2006.01)

(52) U.S. Cl. .............................. 435/287.1; 435/287.2; 435/288.5; 204/403.01

(58) Field of Classification Search ............ 435/287.1, 435/287.2, 288.5; 422/66, 50, 81, 82.01, 422/129; 204/403.01
See application file for complete search history.

(56) References Cited

U.S. PATENT DOCUMENTS

| | | |
|---|---|---|
| 3,346,479 A | 10/1967 | Natelson |
| 3,375,187 A | 3/1968 | Buchler |
| 3,533,933 A | 10/1970 | Strauch |
| 3,539,493 A | 11/1970 | Dorman |
| 3,616,454 A | 10/1971 | Levy et al. |
| 3,627,137 A | 12/1971 | Bier |
| 3,640,813 A | 2/1972 | Nerenberg |
| 3,697,405 A | 10/1972 | Butter et al. |
| 3,773,648 A | 11/1973 | Van Welzen et al. |
| 3,791,950 A | 2/1974 | Allington |
| 3,902,986 A | 9/1975 | Nees |
| 3,950,738 A | 4/1976 | Hayashi et al. ............. 365/185 |
| 3,980,546 A | 9/1976 | Cavacco |
| 3,995,190 A | 11/1976 | Salgo ......................... 313/391 |
| 4,283,773 A | 8/1981 | Daughton et al. .......... 364/132 |
| 4,326,934 A | 4/1982 | Pohl ............................ 204/547 |
| 4,479,861 A | 10/1984 | Hedinger |
| 4,555,731 A | 11/1985 | Zinchuk |
| 4,563,419 A | 1/1986 | Ranki et al. ................... 435/6 |
| 4,572,668 A | 2/1986 | Auth |
| 4,580,895 A | 4/1986 | Patel ........................... 356/39 |
| 4,584,075 A | 4/1986 | Goldstein ................... 204/522 |
| 4,594,135 A | 6/1986 | Goldstein ................... 204/551 |
| 4,617,102 A | 10/1986 | Tomblin et al. |
| 4,699,706 A | 10/1987 | Burd et al. |
| 4,707,235 A | 11/1987 | Englert et al. |
| 4,737,259 A | 4/1988 | Ogawa et al. |
| 4,751,177 A | 6/1988 | Stabinsky ..................... 435/6 |
| 4,787,963 A | 11/1988 | MacConnell ................ 204/450 |

| | | |
|---|---|---|
| 4,807,161 A | 2/1989 | Comfort et al. ............ 364/550 |
| 4,816,418 A | 3/1989 | Mack et al. ................ 436/518 |
| 4,822,566 A | 4/1989 | Newman ..................... 422/82 |
| 4,827,125 A | 5/1989 | Goldstein |
| 4,828,729 A | 5/1989 | Klevan et al. ................. 435/6 |
| 4,877,510 A | 10/1989 | Chen |
| 4,881,107 A | 11/1989 | Matsushita |
| 4,881,812 A | 11/1989 | Ohkubo et al. |
| 4,908,112 A | 3/1990 | Pace ......................... 210/198 |
| 4,936,963 A | 6/1990 | Mandecki et al. |
| 5,063,081 A | 11/1991 | Cozzette et al. ................ 435/4 |
| 5,074,977 A | 12/1991 | Cheung et al. ............. 205/775 |
| 5,075,077 A | 12/1991 | Durley, III et al. ........... 422/56 |
| 5,082,548 A | 1/1992 | Faupel et al. |
| 5,085,756 A | 2/1992 | Swedberg |
| 5,096,669 A | 3/1992 | Lauks et al. .................... 422/61 |
| 5,096,807 A | 3/1992 | Leaback ........................ 435/6 |
| 5,125,748 A | 6/1992 | Bjornson et al. ........... 356/414 |
| 5,126,022 A | 6/1992 | Soane et al. ................ 204/458 |
| 5,143,854 A | 9/1992 | Pirrung et al. .............. 436/518 |
| 5,161,165 A | 11/1992 | Zorabedian |
| 5,164,319 A | 11/1992 | Hafeman et al. ........... 435/287 |
| 5,166,063 A | 11/1992 | Johnson ..................... 435/173 |
| 5,192,980 A | 3/1993 | Dixon et al. |
| 5,194,133 A | 3/1993 | Clark et al. ................. 204/608 |
| 5,200,051 A | 4/1993 | Cozzette et al. ............ 204/403 |
| 5,202,010 A | 4/1993 | Guzman |
| 5,202,231 A | 4/1993 | Drmanac et al. ............... 435/6 |
| 5,209,831 A | 5/1993 | MacConnell |
| 5,217,593 A | 6/1993 | MacConnell |
| 5,219,726 A | 6/1993 | Evans .......................... 435/6 |
| 5,227,265 A | 7/1993 | DeBoer et al. ............... 430/41 |
| 5,229,297 A | 7/1993 | Schnilpelsky et al. |
| 5,234,566 A | 8/1993 | Osman et al. ............. 204/403 |
| 5,242,797 A | 9/1993 | Hirschfeld ..................... 435/6 |
| 5,269,931 A | 12/1993 | Hu et al. |
| 5,296,114 A | 3/1994 | Manz |
| 5,296,703 A | 3/1994 | Tsien |
| 5,304,487 A | 4/1994 | Wilding et al. ............... 435/29 |
| 5,312,527 A | 5/1994 | Mikkelsen et al. ......... 205/777 |
| 5,316,900 A | 5/1994 | Tsujioka et al. |
| 5,324,401 A | 6/1994 | Yeung et al. |
| 5,340,449 A | 8/1994 | Chukla ........................ 204/464 |
| 5,344,535 A | 9/1994 | Betts et al. ................. 204/183 |
| 5,376,249 A | 12/1994 | Afeyan |
| 5,382,511 A | 1/1995 | Stapleton |
| 5,393,401 A | 2/1995 | Knoll |
| 5,427,664 A | 6/1995 | Stoev et al. |
| 5,427,946 A | 6/1995 | Kricka et al. |
| 5,433,819 A | 7/1995 | McMeen ..................... 216/20 |
| 5,434,049 A | 7/1995 | Okano et al. .................... 435/6 |
| 5,436,129 A | 7/1995 | Stapleton ........................ 435/6 |
| 5,445,525 A | 8/1995 | Broadbent et al. ............. 439/64 |
| 5,445,934 A | 8/1995 | Fodor et al. |
| 5,451,500 A | 9/1995 | Stapleton ........................ 435/6 |
| 5,464,517 A | 11/1995 | Hjerten et al. .............. 204/183 |
| 5,468,646 A | 11/1995 | Mattingly ................... 436/501 |
| 5,486,335 A | 1/1996 | Wilding et al. |
| 5,489,506 A | 2/1996 | Crane |
| 5,498,392 A | 3/1996 | Wilding et al. |
| 5,516,698 A | 5/1996 | Begg et al. .................. 436/89 |
| 5,527,670 A | 6/1996 | Stanley ........................... 435/6 |
| 5,545,531 A | 8/1996 | Rava et al. |
| 5,567,617 A | 10/1996 | Caprio et al. |
| 5,569,367 A | 10/1996 | Betts et al. ................. 204/547 |
| 5,587,128 A | 12/1996 | Wilding et al. |
| 5,593,580 A | 1/1997 | Kopf |
| 5,593,838 A | 1/1997 | Zansucchi et al. ............. 435/6 |
| 5,605,662 A | 2/1997 | Heller et al. ................ 422/68 |
| 5,631,734 A | 5/1997 | Stern et al. |
| 5,632,876 A | 5/1997 | Zanzucchi et al. |
| 5,632,957 A | 5/1997 | Heller et al. ................ 422/68 |
| 5,635,358 A | 6/1997 | Wilding et al. |
| 5,637,469 A | 6/1997 | Wilding et al. |
| 5,653,939 A | 8/1997 | Hollis et al. .................... 422/50 |
| 5,660,701 A | 8/1997 | Grushka et al. ............ 204/451 |
| 5,667,667 A | 9/1997 | Southern |
| 5,681,751 A | 10/1997 | Begg et al. .................... 436/89 |
| 5,700,637 A | 12/1997 | Southern |
| 5,726,026 A | 3/1998 | Wilding et al. |
| 5,728,267 A | 3/1998 | Flaherty |
| 5,744,366 A | 4/1998 | Kricka et al. |
| 5,746,978 A | 5/1998 | Bienhaus et al. |
| 5,750,015 A | 5/1998 | Soane et al. ................ 204/454 |
| 5,755,942 A | 5/1998 | Zanzucchi et al. |
| 5,766,960 A | 6/1998 | Cornell et al. |
| 5,788,468 A | 8/1998 | Dewa et al. |
| 5,789,167 A | 8/1998 | Konrad |
| 5,824,204 A | 10/1998 | Jerman |
| 5,849,486 A | 12/1998 | Heller et al. .................... 435/6 |
| 5,856,174 A | 1/1999 | Lipshutz ..................... 435/286 |
| 5,858,195 A | 1/1999 | Ramsey |
| 5,858,804 A | 1/1999 | Zanzucchi et al. |
| 5,863,502 A | 1/1999 | Southgate et al. |
| 5,863,708 A | 1/1999 | Zanzucchi et al. |
| 5,879,632 A | 3/1999 | Demers |
| 5,882,903 A | 3/1999 | Andrevski et al. |
| 5,891,630 A | 4/1999 | Eggers et al. |
| 5,922,591 A | 7/1999 | Anderson .................... 435/287 |
| 5,939,291 A | 8/1999 | Loewy et al. |
| 5,958,344 A | 9/1999 | Levine et al. |
| 6,007,690 A | 12/1999 | Nelson et al. |
| 6,013,166 A | 1/2000 | Heller ........................ 204/469 |
| 6,017,696 A | 1/2000 | Heller et al. .................... 435/6 |
| 6,048,690 A | 4/2000 | Heller et al. |
| 6,051,380 A | 4/2000 | Sosnowski et al. |
| 6,054,270 A | 4/2000 | Southern |
| 6,071,394 A * | 6/2000 | Cheng et al. ............... 204/547 |
| 6,258,606 B1 | 7/2001 | Kovacs |
| 6,264,815 B1 | 7/2001 | Pethig et al. |
| 6,280,590 B1 | 8/2001 | Cheng et al. |
| 6,326,211 B1 | 12/2001 | Anderson et al. |
| 6,395,489 B1 | 5/2002 | Stanley |
| 6,403,367 B1 * | 6/2002 | Cheng et al. ............. 435/287.1 |

FOREIGN PATENT DOCUMENTS

| | | |
|---|---|---|
| EP | 0228075 | 7/1987 |
| GB | 2156074 | 10/1985 |
| GB | 2247889 | 3/1992 |
| WO | WO86/03782 | 7/1986 |
| WO | WO88/08528 | 11/1988 |
| WO | WO89/01159 | 2/1989 |
| WO | WO89/10977 | 11/1989 |
| WO | WO90/01564 | 2/1990 |
| WO | WO92/04470 | 3/1992 |
| WO | WO93/22678 | 11/1993 |
| WO | WO95/07363 | 3/1995 |
| WO | WO96/01836 | 1/1996 |
| WO | WO98/01758 | 1/1998 |
| WO | WO98/51819 | 11/1998 |
| YU | 57087 | 8/1912 |

OTHER PUBLICATIONS

Abrams et al. "Comprehensive Detection of Single Base Changes In Human Genomic DNA Using Denaturing Gradient Gel Electrophoresis & a GC Clamp". *Genomics*, 7, 1990, 463-475.

Anand and Southern "Pulsed Field Gel Electrophoresis," *Gel Electrophoresis of Nucleic Acids—A Practical Approach*, 2d. Ed., D. Rickwood and B.D. Hames (New York:IRL Press 1990), pp. 101-123.

Anderson and Young, "Quantitative Filter Hybridization," *Nucleic Acid Hybridization—A Practical Approach*, Eds. B.D. Hames and S.J. Higgins (Washington, D.C. :IRL Press 1985) pp. 73-111.

Bains, "Setting a Sequence to Sequence a Sequence," *Bio/Technology*, 10:757-758 (1992).

Barinaga, "Will 'DNA Chip' Speed Genome Initiative?", *Science*, 253:1489 (1991).
Beattie et al., "Genosensor Technology," *The 1992 San Diego Conference: Genetic Recognition*, pp. 1-5 (Nov. 1992).
Beltz et al., "Isolation of Multigene Families and Determination of Homologies by Filter Hybridization Methods," *Methods in Enzymology*, 100:266-285 (1983).
Brown et al. "Electrochemically Induced Adsorption of Radio-Labelled DNA on Gold and HOPG Substrates for STM Investigations". *Ultramicroscopy*, 38, 1991, 253-264.
Burns, et al., "An integrated nanoliter DNA analysis device", *Science*, 282, pp. 484-487, 1998.
Conner et al., "Detection of Sickle Cell $\beta^3$-Globin Allele by Hybridization With Synthetic Oligonucleotides," *Proc. Natl. Acad. Sci. USA*, 80:278-282 (1983).
Drmanac et al., "Sequencing of Megabase Plus DNA by Hybridization: Theory of the Method," *Genomics*, 4:114-128 (1989).
Drmanac et al., "DNA Sequence Determination by Hybridixation: A Strategy for Efficient Large-Scale Sequencing," *Science*, 260: 1649-1652 (1993).
Eggers et al. "Biochip Technology Development", BioChip Technology Development, Lincoln Laboratory Technical Report 901, Nov. 9, 1990.
Fiaccabrino et al., "Array of Individually Addressable Microeletrodes", *Sensors and Actuators B*, 18-19 (1994) 675-677.
Fodor et al., "Multiplexed Biochemical Assays With Biological Chips," *Nature*, 364:555-556 (1993).
Fodor et al., "Light-Directed, Spatially Addressable Parallel Chemical Synthesis," *Science*, 251:767-773 (1992).
Gilles et al., "Single Nucleotide Polymorphic Discrimination by an Electronic Dot Blot Assay on Semiconductor Microchips," *Nature Biotechnology*, Apr. 1999, vol. 17, pp. 365-370.
Gryaznov et al., Enhancement of Selectivity in Recognition of Nucleic Acids Via Chemical Autoligation, Nucleic Acids Research, 1994, vol. 22, No. 12, pp. 2366-2369.
Horejsi, "Some Theoretical Aspects of Affinity Electrophoresis," *Journal of Chromatography*, 178:1-13 (1979).
Horejsi et al., Determination of Dissociation Constants of Lectin Sugar Complexes by Means of Affinity Electrophoresis, *Biochimica at Biophysica Acta*, 499:200-300 (1977).
Jacobson, et al., "Integrated microdevice for DNA restriction fragment analysis," *Anal. Chem.*, 68, pp. 720-723, 1996.
Kakerow et al., "A Monolithic Sensor Array of Individually Addressable Microelectrodes", *Sensors and Actuators A*, 43 (1994) 296-301.
Li et al., "Transport, manipulation, and reaction of biological cells on-chip using electrokinetic effects," *Anal. Chem.*, 69, pp. 1564-1568, 1997.
Manz et al., in "Miniaturized Total Chemical Analysis System: A Novel Concept For Chemical Sensing", *Sensors and Actuators*, B1 (1990), pp. 244-248.
Mathews, Kricka. "Analytical Strategies For The Use Of DNA Probes". *Analytical Biochemistry*, 169, 1988, 1-25.
Palecek. "New Trends in Electrochemical Analysis of Nucleic Acids". *Bioelectrochemistry and Bioenergetics*, 20, 1988, 179-194.
Ranki et al., "Sandwich Hybridization as a Convenient Method for the Detection of Nucleic Acids in Crude Samples," *Gene*, 21:77-85 (1983).
Saiki, "Amplification Genomic DNA," *PCR Protocols: A Guide to Methods and Applications*, (Academic Press, Inc. 1990), pp. 13-20.
Sosnowski et al., "Rapid Determination of Single Base Mismatch Mutation in DNA Hybrids by Direct Electric Field Control," *Proc. Natl. Acad. Sci. USA*, Feb. 1997, vol. 93, pp. 1119-1123.
Southern et al., "Analyzing and Comparing Nucleic Acid Sequences by Hybridization to Arrays of Oligonucleotides Evaluation Using Experimental Models," *Genomics*, 13:1008-1017 (1992).
Strezoska et al., "DNA Sequencing by Hybridization: 100 Bases Read by a Non-Gel-Based Method", *Proc. Natl. Acad. Sci. USA*, 88:10089-93 (1991).
Wallace et al., "Hybridization of Synthetic Oligodexribonucleotides to φ x 174 DNA: The Effect of Single Base Pair Mismatch," *Nucleic Acid Res.*, 6:3543-3557 (1979).
Washizu, "Electrostatic Manipulation of Biological Objects," *Journal of Electrostatics*, 25:109-123 (1990).
Washizu and Kurosawa, "Electrostatic Manipulation of DNA in Microfabricated Structures," *IEEE Transactions on Industry Applications*, 26:1165-1172 (1990).
Waters et al., "Microchip device for cell lysis, multiplex PCR amplification, and electrophoretic sizing," *Anal. Chem.*, 70, pp. 158-162, 1998.
Wilding et al., "Integrated cell isolation and PCR analysis using silicon microfilter-chambers", *Anal. Biochem.*, 257, pp. 95-100, 1998.
Woolley et al., "Functional integration of PCR amplification and capillary electrophoresis in a microfabricated DNA analysis device," *Anal. Chem.*, 68, pp. 4081-4086, 1996.
Cheng et al., Isolation Of Cultured Cervical Carcinoma Cells Mixed With Peripheral Blood Cells On A Bioelectronic Chip, Analytical Chemistry, 70, 11, 1998, 2321-2326.
Cheng et al., Preparation & Hybridization Analysis Of DNA/RNA From E. Coli On Microfabricated Bioelectronic Chips, Nature Biotechnology, 16, 1998, 541-546.
Sato et al., Individual & Mass Operation Of Biological Cells Using Micromechanical Silicon Devices, Sensors & Actuators, A 21, A23, 1990, 948-953.
Scanning Laser Microscopy Lab, website printout, http://www.science.unwaterloo.ca/research-groups/confocal, 1997.
Wilson et al., Theory & Practice Of Scanning Optical Microscopy, Academic Press, 1984 (ISBN-0-12-757760-2).

\* cited by examiner

*Primary Examiner*—David Redding
(74) *Attorney, Agent, or Firm*—O'Melveny & Myers LLP

(57) ABSTRACT

We have performed separation of bacterial and cancer cells from peripheral human blood in microfabricated electronic chips by dielectrophoresis. The isolated cells were examined by staining the nuclei with fluorescent dye followed by laser induced fluorescence imaging. We have also released DNA and RNA from the isolated cells electronically and detected specific marker sequences by DNA amplification followed by electronic hybridization to immobilized capture probes. Efforts towards the construction of a "laboratory-on-a-chip" system are presented which involves the selection of DNA probes, dyes, reagents and prototyping of the fully integrated portable instrument.

23 Claims, 20 Drawing Sheets

INTEGRATED PORTABLE BIOLOGICAL DETECTION SYSTEM

CROSS-REFERENCE TO RELATED APPLICATIONS

This application is a continuation of application Ser. No. 09/470,448, filed Dec. 22, 1999 now U.S. Pat. No. 6,403,367, entitled "Integrated Portable Biological Detection System", which claims benefit of Provisional Patent Application Ser. No. 60/113,730, filed Dec. 23, 1998, entitled "Fluorescent Imaging of Cells and Nucleic Acids in Bioelectronic Chips", and is a continuation-in-part of application Ser. No. 09/016,596, filed on Jan. 30, 1998, entitled "Channel-Less Separation of Bioparticles on a Bioelectronic Chip by Dielectrophoresis", now issued as U.S. Pat. No. 6,071,394, which is a continuation in part of application Ser. No. 08/709,358, filed on Sep. 6, 1996, entitled "Apparatus and Methods for Active Biological Sample Preparation", now issued as U.S. Pat. No. 6,129,828, and is a continuation-in-part of application Ser. No. 08/986,065, filed on Dec. 5, 1997, entitled "Methods and Procedures for Molecular Biological Analysis and Diagnostics", now issued as U.S. Pat. No. 6,051,380, which is a continuation-in-part of application Ser. No. 08/534,454, filed Sep. 27, 1995, entitled "Methods for Hybridization Analysis Utilizing Electrically Controlled Hybridization", now issued as U.S. Pat. No. 5,849,486, which is a continuation-in-part of application Ser. No. 08/304,657, filed Sep. 9, 1994, entitled "Molecular Biological Diagnostic Systems Including Electrodes", now issued as U.S. Pat. No. 5,632,957, which is a continuation-in-part of application Ser. No. 08/271,882, filed Jul. 7, 1994, entitled "Methods for Electronic Stringency Control for Molecular Biological Analysis and Diagnostics", now issued as U.S. Pat. No. 6,017,696, the specifications of which are hereby expressly and fully incorporated by reference as if fully set forth herein.

GOVERNMENT SUPPORT

The Government has rights in this invention pursuant to Grant No. ATP: 70NANB7H3001 awarded by the Advanced Technology Program.

FIELD OF THE INVENTION

This invention relates to devices and methods for performing active, multi-step sample preparation and molecular diagnostic analysis of biological materials. More particularly, it relates to integrated, compact, portable devices for self-contained sample to answer systems. Specifically, this invention relates to a device and method for performing multi-step sample preparation and assay on either two or even a single microchip. Examples of applications for this integrated system include food and/or quality monitoring, diagnosis of infectious diseases and cancers, bone marrow plastesis (e.g., stem cell separation and analysis), and genetics-based identification of individuals for forensic purposes.

BACKGROUND OF THE INVENTION

The following description provides a summary of information relevant to the present invention. It is not an admission that any of the information provided herein is prior art to the presently claimed invention, nor that any of the publications specifically or implicitly referenced are prior art to the invention.

Generally, analysis of biological-derived sample materials cannot occur until the sample is processed through numerous pre-analysis steps. Often, the preparation process is time consuming and laborious. For example, many immuno and molecular-biological diagnostic assays on clinical samples, such as blood or tissue cells, require separation of the molecules of interest from the crude sample by disrupting or lysing the cells to release such molecules including proteins and nucleic acids (i.e., DNA and RNA) of interest, followed by purification of such proteins and/or nucleic acids. Only after performing processing steps can analysis of the molecules of interest begin. Additionally, protocols used for the actual analysis of the samples require numerous more steps before useful data is obtained.

For example, charged and uncharged microparticles in solution (such as cellular material or crude extracts of protein or nucleic acids thereof) may be separated by dielectrophoresis. On a microscale, dielectrophoresis can be performed using a glass slide-based device having exposed, i.e., naked, interdigitated electrodes plated on the surface of the slide and having a flow chamber with a volume of several hundred microliters. With such a device, cells, proteins, and nucleic acids can be separated based on their respective dielectric properties by using separation buffers having appropriate conductivity and an AC signal with a suitable amplitude and frequency. Such devices, however, have several problems including the nonspecific binding of both separated and unseparated cells to exposed portions of the glass surface and the electrodes. Such devices are also problematic in that the flow chamber volume (several hundred microliters) is so large that thermal convection can disturb and push materials such as cells and large molecules initially attracted to and retained by the electrodes off of the electrodes. Additionally, undesired cells and molecules are not easily washed off the surface without disturbing and loosing the desired cells as such cells and molecules can interfere with fluidic flow and, hence, block the flow during wash steps.

Conventional methods to disrupt whole cells for the release of proteins and nucleic acids have employed the use of a series of high voltage DC pulses in a macrodevice, as opposed to a microchip-based device. Such conventional electronic lysis techniques have several problems. For example, some commercial macro-devices use lysis conditions that do not release high molecular weight (larger than 20 Kb) nucleic acids because the high molecular weight molecules can not fit through pores created in the cell membranes using such methods. Additionally, released nucleic acids are often lost due to their non-specific binding to the surface of the lysis chamber. Such loss of material, especially when molecules of interest are in low concentration, is further compounded by the fact that the dielectrophoretic cell separation macro-device systems are stand alone systems allowing for loss of sample in the transfer of material from one device to the other as sample preparation is carried forward.

Processing of the crude lysate often requires chemical reactions to remove undesired cellular components from the specifically desired ones. These reactions typically include subjecting the lysate to enzymatic reactions such as proteinase K and restriction enzymes or nucleases. Processing can also include enhancing the presence of desired molecules, particularly nucleic acids, by performing amplification reactions such as by strand displacement amplification (SDA) or polymerase chain reaction (PCR) methodologies. These reactions are also carried out in stand-alone processes. Only after these sample preparation and processing steps can assaying for data retrieval begin. Because of the numerous steps between sample collection and assay, many a technique is limited in its application by a lack of sensitivity, specificity, or reproducibility.

Attempts have been made to use dielectrophoresis to separate and identify whole cells. For example, U.S. Pat. No. 4,326,934 to Pohl discloses a method and apparatus for cell classification by continuous dielectrophoresis. With such method cells are separated by making use of both the positive and negative dielectrophoretic movement of cell particles. Separated cells are allowed to be characterized and/or classified by viewing the characteristic deflection distance of cells moving through the positive and negative electrodes.

In another example, U.S. Pat. No. 5,344,535 to Belts et al. discloses a method and apparatus for the characterization of micro-organisms and other particles by dielectrophoresis. In this system, cells are characterized by matching their signature dielectrophoretic collection rates.

In yet another example, U.S. Pat. No. 5,569,367 to Belts et al. discloses a method and apparatus for separating a mixture of cells using a pair of energized interdigitated electrodes comprised of interweaved grid-like structures arranged to obstruct flow of cells through the apparatus and cause differentiation of cell types into fractions by applying a non-uniform alternating field.

In addition, other attempts have been made to combine certain processing steps or substeps together. For example, various microbotic systems have been proposed for preparing arrays of DNA probes on a support material. Beattie et al., disclose in "The 1992 San Diego Conference: Genetic Recognition", November, 1992, use of a microrobotic system to deposit micro-droplets containing specific DNA sequences into individual microfabricated sample wells on a glass substrate.

Various other attempts have been made to describe integrated systems formed on a single chip or substrate, wherein multiple steps of an overall sample preparation and diagnostic system would be included. A. Manz et al., in "Miniaturized Total Chemical Analysis System: A Novel Concept For Chemical Sensing", *Sensors And Actuators*, B1 (1990), pp. 244–248, describe a 'total chemical analysis system' (TAS) that comprises a modular construction of a miniaturized TAS. In that system, sample transport, chemical reactions, chromatographic separations and detection were to be automatically carried out.

Yet another proposed integrated system by Stapleton, U.S. Pat. No. 5,451,500, a system for automated detection of target nucleic acid sequences is described. In this system multiple biological samples are individually incorporated into matrices containing carriers in a two-dimensional format.

Various multiple electrode systems are also disclosed which purport to perform multiple aspects of biological sample preparation or analysis. Pace, U.S. Pat. No. 4,908,112, entitled "Silicon Semiconductor Wafer for Analyzing Micronic Biological Samples" describes an analytical separation device in which a capillary-sized conduit is formed by a channel in a semiconductor device, wherein electrodes are positioned in the channel to activate motion of liquids through the conduit. Additionally, Soane et al., in U.S. Pat. No. 5,126,022, entitled "Method and Device for Moving Molecules by the Application of a Plurality of Electrical Fields", describes a system by which materials are moved through trenches by application of electric potentials to electrodes in which selected components may be guided to various trenches filled with antigen-antibodies reactive with given charged particles being moved in the medium or moved into contact with complementary components, dyes, fluorescent tags, radiolabels, enzyme-specific tags or other types of chemicals for any number of purposes such as various transformations which are either physical or chemical in nature. Further, Clark, et al. in U.S. Pat. No. 5,194,133, entitled "Sensor Devices", discloses a sensor device for the analysis of a sample fluid which includes a substrate having a surface in which is formed an elongate micro-machined channel containing a material, such as starch, agarose, alginate, carrageenan or polyacrylamide polymer gel, for causing separation of the sample fluid as the fluid passes along the channel. The biological material may comprise, for example, a binding protein, an antibody, a lectin, an enzyme, a sequence of enzymes, or a lipid.

Various devices for eluting DNA from various surfaces are known. For example, Shukla U.S. Pat. No. 5,340,449, entitled "Apparatus for Electroelution" describes a system and method for the elution of macromolecules such as proteins and nucleic acids from solid phase matrix materials such as polyacrylamide, agarose and membranes such as PVDF in an electric field. Materials are eluted from the solid phase into a volume defined in part by molecular weight cut-off membranes. Also, Okano, et al. in U.S. Pat. No. 5,434,049, entitled "Separation of Polynucleotides Using Supports Having a Plurality of Electrode-Containing Cells" discloses a method for detecting a plurality of target polynucleotides in a sample, the method including the step of applying a potential to individual chambers so as to serve as electrodes to elute captured target polynucleotides, the eluted material is then available for collection.

Other devices for performing nucleic acid diagnosis have been designed wherein at least two reaction chambers are necessary for carryout the sample preparation and analysis such as R. Lipshutz, et al., entitled "Integrated Nucleic Acid Diagnostic Device" (U.S. Pat. No. 5,856,174) and R. Anderson, et al., entitled "Integrated Nucleic Acid Diagnostic Device", (U.S. Pat. No. 5,922,591).

Still other achievements have been made toward partial integration of a complete sample handling system such as P. Wilding, et al., "Integrated cell isolation and PCR analysis using silicon microfilter-chambers," *Anal. Biochem.* 257, pp. 95–100, 1998; and P. C. H. Li and D. J. Harrison, "Transport, manipulation, and reaction of biological cells on-chip using electrokinetic effects," *Anal. Chem.*, 69, pp. 1564–1568, 1997.

Still others have attempted to integrate chemical reactions with detection such as M. A. Burns, et al., "An integrated nanoliter DNA analysis device," *Science*, 282, pp. 484–487, 1998; S. C. Jacobson and J. M. Ramsey, "Integrated microdevice for DNA restriction fragment analysis," *Anal. Chem.*, 68, pp. 720–723, 1996; L. C. Waters, et al., "Microchip device for cell lysis, multiplex PCR amplification, and electrophoretic sizing," *Anal. Chem.*, 70, pp. 158–162, 1998; and A. T. Woolley, et al., "Functional integration of PCR amplification and capillary electrophoresis in a microfabricated DNA analysis device," *Anal. Chem.*, 68, pp. 4081–4086, 1996.

Generally, as is understandable from the forgoing examples, systems and methods have been described that do not fully provide for a completely integrated self-contained sample to answer system that uses electronically active microchips. Moreover, numerous of the described systems are extremely labor and time intensive requiring multiple steps and human intervention either during the process or between processes which together are suboptimal allowing for loss of sample, contamination, and operator error. Further, the use of multiple processing steps using multiple machines or complicated robotic systems for performing the individual processes is often prohibitive except for the largest laboratories, both in terms of the expense and physical space requirements. For the reasons stated above, these techniques are limited and lacking. They are not easily combined to form a system that can carry out a complete self-contained integrated diagnostic assay, particularly assays for data retrieval for nucleic acids and protein-derived information, on a single electronically addressable microchip. Despite the long-recognized need for such an integrated system without a complicated fluidics and inadequate valve systems, no satisfactory solution has previously been proposed. There is therefore a continuing need for methods and devices which lead to improved dielectrophoretic separation of biological cells as well as improved biological stability of the separated cells and further a continuing need for methods and devices which improve cell preparation and analysis, and which are capable of integrating cell separation, preparation, purification, and analysis in a single self-contained system without complicated fluidics.

SUMMARY OF THE INVENTION

Accordingly, provided herein are integrated, portable systems, devices, and methods for performing active, integrated multi-step sample preparation and molecular diagnostic analysis of biological samples using electronically addressable microchips.

In one aspect of the present invention, an integrated system for the analysis of eukaroytic and/or prokaryotic cells in a biological sample is provided. The system comprises an electronic system for cell separation, cell lysis, sample preparation, and sample analysis further comprising a flow cell, an input port coupled to the flow cell, an output port coupled to the flow cell, a plurality of individually addressable electrodes positioned within the flow cell and coupled to a power source configured to electronically disrupt cell membranes within the sample, and an array of probes coupled to the electrodes and adapted to bind to predetermined components within the sample for analysis of the components, and a heating element coupled to the flow cell, wherein the flow cell is adapted to receive the sample via the input. The system further includes a detector operatively positioned to detect the molecules bound to the probes by a detectable signal, a power source coupled to the flow cell, and a portable housing configured to contain the electronic system, the detector, and the power source.

The system may include an illumination source operatively positioned to direct radiation to the probes. In one embodiment, the illumination source is a laser, and the system further comprises a beam splitter. This system may also comprise a desalting column coupled to the flow cell. The desalting column may be configured to introduce a buffer into the flow cell.

The electronic system may include a permeation layer overlaying the electrodes, and the probes may be coupled to the permeation layer. Additionally, in one embodiment, the electrodes are addressable to form a square-wall dielectric force pattern. Alternatively, in another embodiment, the electrodes are addressable to form a checkerboard dielectric force pattern. The system may also include a wave form generator coupled to the electrodes. The electronic system may also include first and second flow cells, wherein the first flow cell is configured for sample preparation, and the second flow cell is configured for sample analysis. Furthermore, a computer may be coupled to the portable housing and located outside of the portable housing.

In another aspect of the present invention, a method for performing an analysis of a biological sample having desired cells and undesired cells using an integrated portable system comprising a flow cell, a plurality of individually addressable electrodes positioned within the flow cell, and a portable housing containing the flow cell is provided. The sample may be introduced into the flow cell via an input port coupled to the flow cell. A dielectric force pattern may be created by individually biasing the electrodes positioned within the flow cell. The sample may then be subjected to the dielectric force pattern in order to separate the undesired cells from the desired cells in the sample. Then, the desired cells may be isolated by maintaining an attractive bias for the desired cells and introducing a flow of wash buffer through the flow cell via the input port to eliminate the undesired cells. Here, the undesired cells may be removed from the flow cell via an output port coupled to the flow cell. The desired cells may be lysed by applying an electric force within the flow cell to electronically disrupt the desired cells into a plurality of components. The components of the desired cells may then be analyzed by hybridizing the components with probes to form probe-target hybrids within the flow cell, and detecting the probe-target hybrids while the hybrids are within the flow cell, wherein the probes are coupled to the electrodes.

In one embodiment, the attractive bias maintained during the isolating the desired cells step comprises a square-wall dielectric force pattern. In another embodiment, the attractive bias maintained during the isolating the desired cells step comprises a checkerboard dielectric force pattern.

The isolation of the desired cells may be accomplished by generating a dielectric force pattern having a plurality of field maxima and a plurality of field minima, wherein the attractive bias comprises the field maxima, and the undesired cells collect at the field minima.

Creating a dielectric force pattern may be performed by biasing all of the individual electrodes as a single array. Alternatively, creating a dielectric force pattern may be performed by biasing the individual electrodes as a plurality of subarrays, wherein each subarray may be used for a function such as, e.g., cell separation, cell lysis, or cell analysis.

After lysing the desired cells, the desired cells may be purified by introducing a protease into the flow cell via the input port, maintaining a temperature of substantially 60° C. in the flow cell to treat the desired cells with the protease, and maintaining a temperature of substantially 95° C. in the flow cell to inactivate the protease after treating the desired cells with the protease. Maintaining a temperature may be accomplished using a heat element coupled to the flow cell and contained within the portable housing. Additionally, the purified desired cells may be treated with an enzyme to release a specific protein of interest from the desired cells. Here, the enzyme may be introduced into the flow cell via the input port. The specific protein of interest may then be amplified and labeled with a marker. Amplifying the specific protein of interest may be accomplished by suitable methods such as, e.g., PCR, or SDA.

The method may also include the detection of the probe-target hybrids by using fluorophore-labeled reporter probes and an optical imaging system configured to detect the reporter probes.

In another aspect of the present invention, a method for performing an analysis of a biological sample having desired cells and undesired cells using an integrated portable system is provided. An integrated portable system comprising an electronic system having a flow cell, a plurality of individually addressable electrodes positioned within the flow cell, a plurality of probes coupled to the electrodes, a detector configured to detect the probes, a power source coupled to the flow cell, and a portable housing containing the electronic system, the detector, and the power source may be provided. The sample may be introduced into the integrated portable system by injecting the sample into the flow cell via an input port coupled to the flow cell. The input port may be accessed through the portable housing. A dielectric force pattern may be created by individually biasing the electrodes positioned within the flow cell. The sample may be subject to the dielectric force pattern in order to separate the undesired cells from the desired cells in the sample. The desired cells may be isolated by maintaining an attractive bias for the desired cells and introducing a flow of wash buffer through the flow cell via the input port to eliminate the undesired cells. The undesired cells may be removed from the flow cell via an output port coupled to the flow cell. The desired cells may be lysed by applying an electric force within the flow cell to electronically disrupt the desired cells into a plurality of components. The components of the desired cells may then be analyzed by hybridizing the components with probes to form probe-target hybrids within the flow cell, and then detecting the probe-target hybrids while the hybrids are within the flow cell.

Regardless of the embodiment, the systems and methods of the invention generally provide the ability to (1) separate eukaryotic cell types from one another as well as eukaryotic cell types from prokarotic cell types, (2) directly process the sample materials from a crude state to a more refined state, and (3) directly analyze the sample materials on the microchip grid. Such an ability is possible by the novel use of electronic biasing at one level of voltage in the form of a dielectric current to cause dielectrophoresis of cells, followed by an increase in voltage to lyse captured cells, followed in turn by changing the manner of biasing from an alternating current mode to direct current mode for the addressing of specific electrodes on the arrays of the flow cell(s) to cause the transport of molecules of interest for capture/hybridization to probes previously bound to the electrode array. The present invention further contemplates that other appropriate sample preparation reagents may be transported to and away from the flow cell(s) by simplified arrangement of tubing and solenoid operated valves and pump. Additionally, in embodiments having a first flow chamber that is without a microchip, the system contemplates the ability to directly lyse the cells in the sample and analyze materials of interest without a need for separating the cell types. In such embodiment, the flow cell has a heating element that can be used to raise the temperature for direct lysis of the cells in the sample. Following such lysis, sample preparation steps such as protease treatment or nucleic acid amplification may be performed followed by transporting the amplified species to the second flow cell containing the electronically addressable microchip.

Also, numerous techniques can be performed in the preparation of molecules of interest including, but not limited to, enzymatic treatment using protease K to remove proteinaceous materials from nucleic acids of interest, enzymatic treatment using nucleases to remove nucleic acids from proteins, digestive residue adsorption, nucleic acid amplification (e.g., by PCR and SDA), in situ buffer exchange and binding of antibodies or other protein-protein binding reactions such as receptor-ligand or enzyme-substrate for binding to proteins of interest.

Analysis of prepared sample materials can also comprise any number of preselected hybridization formats. For example, nucleic acids of interest may be hybridized selectively through an electronically directed process as is known to those skilled in the art of electronically addressable microchips. Such hybridization formats comprise binding of nucleic acids (RNA, DNA, pNA) to probes anchored to the microarray. Other formats contemplated for use with the systems and methods of the present invention include selective capture of proteins of interest such as by antibody or other protein binding probes attached to the electronic grid. These can include other protein-protein interactions such as receptor-ligand and enzyme-substrate binding.

The present invention also contemplates the use of elements (e.g. buffer vials, tubing, miniature solenoid valves, and at least one pump) for carrying and transporting samples, buffers, enzymes and reagents to and from said flow cell(s). Additionally, other elements that may be used with the present invention include a battery operated diode laser (preferably having a wavelength of 635 nm), LEDs, and a CCD camera coupled with filters and zoom lens for astronomy of the individual electrodes of the microchip grid(s) of the first and/or second flow cell chamber(s). Still other methods of detection are also contemplated not requiring illumination with a light emitting device such as direct electrochemical detection as is well known by those in the art of such detection as described in P. Ropp and H. Holden Thorp, *Chemistry & Biology,* 1999, Vol. 6, No.9, pp. 599–605. Each of these electronic components are further contemplated to be coordinated through a computer and appropriate programming software as is well understood by those skilled in the electronic arts.

BRIEF DESCRIPTION OF THE DRAWINGS

The invention will be further described with reference to the accompanying drawings in which:

FIGS. 14 and 15 show such separation for square-wall and checkerboard patterns respectively. FIGS. 16 and 17 show separated bacteria after washing square-wall and checkerboard patterns respectively.

In FIG. 19, from left to right, lanes 1 and 6 are size markers, lanes 2 and 3 are negative and positive controls respectively, lane 5 is the result of an amplification of inv A gene specific DNA sequence amplified using the device of the invention. In FIG. 20 lane 2 is a marker, lanes 1 and 4 are positive and negative controls respectively, and lane 3 is the amplification result for the spa Q gene.

DETAILED DESCRIPTION OF THE PREFERRED EMBODIMENTS

Referring now to specific embodiments of the invention, a portable lab-on-a-chip system is provided wherein a sample may be processed and analyzed in at least a single flow cell comprising an electronically addressable microchip. The elements of the device are housed in a portable casing or housing which contains the sample preparation and analysis flow chamber, fluid handling systems, and illumination source (such as a battery operated 635 nm diode laser) and detection electronics (such as a CCD camera coupled with a set of filters and a zoom lens for astronomy of the microchip). External to the portable casing is a computer, such as a personal computer connected to the portable housing by a cable.

Figure 1:
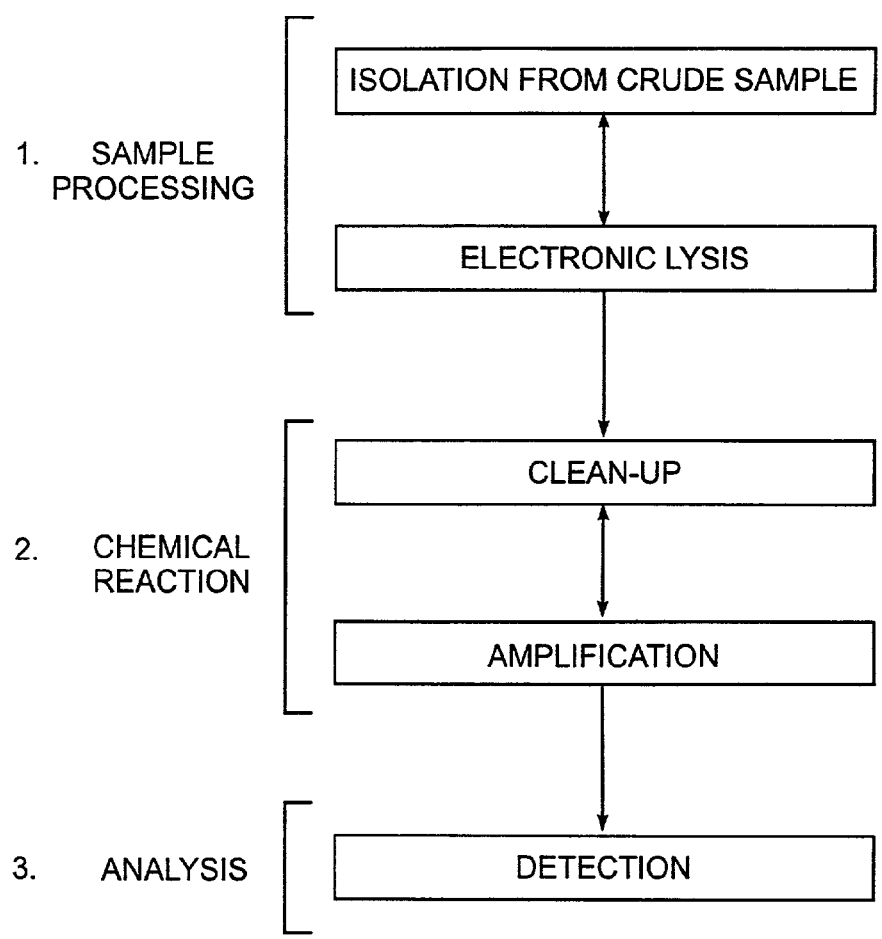
FIG. 1 is a simplified flow chart of the system showing three basic stages of the system including sample preparation, chemical reaction and analyte detection.

Referring now to FIG. 1, a flow chart is shown depicting three distinct sample handling stages for carrying out bioassays as contemplated using the lab-on-a-chip system of the invention. These are: (1) sample processing, (2) chemical reaction, and (3) analyte detection.

Sample handling in stage (1) processing generally comprises processing of crude biological samples (e.g., cells from blood, urine, stool, mixed cell populations, etc.) for the purpose of isolating molecules of interest such as nucleic acids and proteins. Sample handling at the chemical reaction stage (2) involves potentially many types of molecular biological reactions for clean-up and further isolation, purification, or amplification of molecules of interest including, but not limited to, enzymatic-based reactions such a treatment with proteases, nucleases and restriction enzyme digestion, PCR and SDA-based nucleic acid amplification, in situ buffer exchanges, chemical labeling such as by radioisotope and fluorescence markers, and immuno-based and protein-protein reactions such as antibody-antigen, ligand-receptor, and enzyme-substrate reactions. Sample handling at the analyte detection stage (3) may be accomplished through numerous formats including optical detection of fluorescent emissions, electrochemical detection, and radioisotope detection. In a preferred embodiment, this detection comprises hybridization of nucleic acids or captured proteins to the electronic grid and detection using fluorescent imaging.

Figure 2:
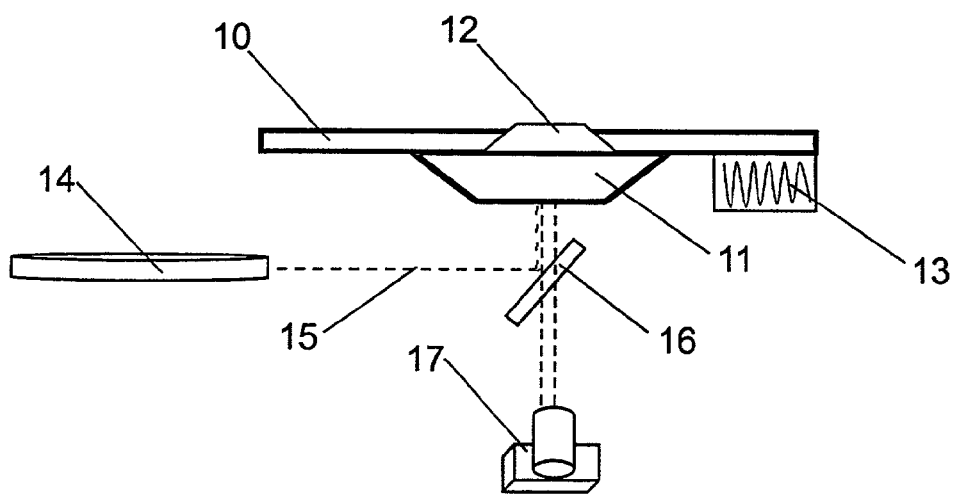
FIG. 2 is a schematic showing the simple overall hardware design of the system wherein there is included a flow chamber 11 with heating element 12, a miniature desalting column 13, a laser 14 with optical path 15, and a detector such as a CCD camera 17.

In FIG. 2, the system is depicted in schematic form showing a top-down or edgewise view of the basic components. In this diagram a support 10 is used to mount the flow cell 11. On the backside of the flow cell 11 mounted to the support is a heating element 12. Additionally, the flow cell may be connected via a hollow fiber to ports and to a desalting column 13 in order to purify, desalt and introduce different buffers into the flow stream. The heating element may be used to heat the flow cell for either direct heat-induced lysis of cells in the chamber or for use in stage 2 process reactions such as inhibiting enzymes and temperature cycling for nucleic acid amplification.

As will be understood by one of skill in the art, the flow cell, as well as the other electrically operated components, such as solenoid operated valves and pumps, laser and detection camera, are interconnected electronically with the computer 20 by cabling 19 to the housing 18 for all programming and control purposes. By way of example, the power source and computer are connected to the electrodes of the flow cell 11 for programming and manipulation. In the preferred embodiment, the electronic signals that may be generated by the computer software used with the system include an AC component, such as where the AC component is sinusoidal and used in dielectrophoresis, and such as where a DC component is square and used in hybridization. In yet a further aspect, it is preferred that a time varying electronic signal also used in the system includes an offset signal, such as where the offset signal is a DC signal.

FIG. 2 further shows illumination source 14 that emits a laser beam 15. Preferably, the illumination source 14 is a diode laser. The beam 15 is preferably incident on a beam splitter 16 that directs at least a portion of the beam 15 towards the flow cell 11 microchip for sample analysis. Radiation emitted from the microchip grid electrodes retraces the incident path, and at least a portion of that radiation is passed through the beam splitter 16 to detector 17. In the preferred embodiment, the detector 17 comprises a charged coupled device (CCD) detector. Alternatively, other detectors may be utilized. However, for compactness, it is preferred to have a detector which generally has relatively larger area coverage compared to its depth (in the direction of the emitted radiation).

Figure 3:
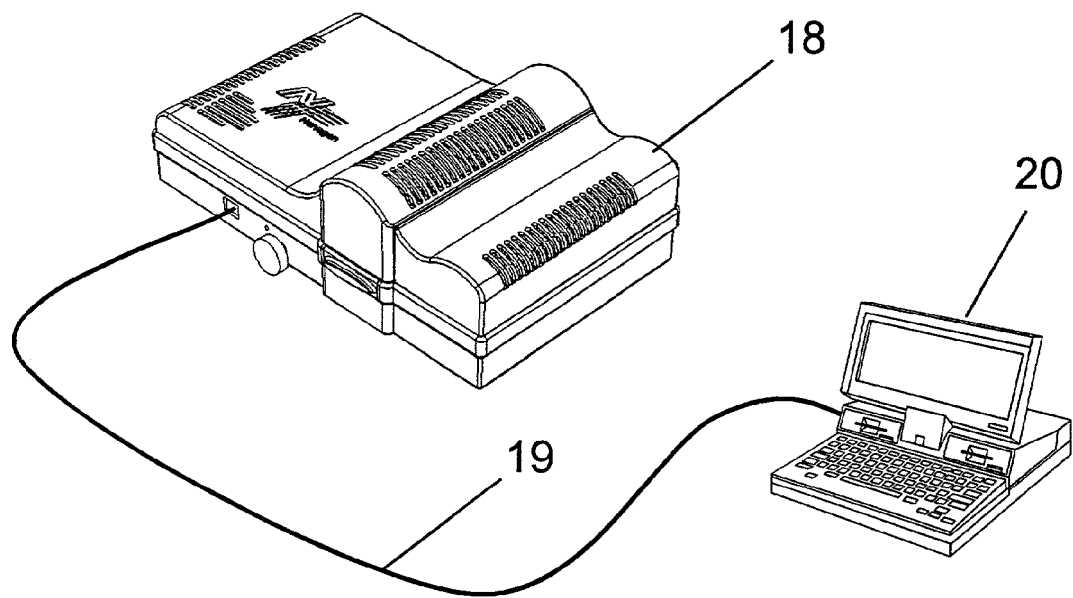
FIG. 3 is a perspective view showing one example of an external design for the portable system of this invention. The portable system comprises a housing 18 integrated with a computer and monitor 20 via a cable 19.
Figure 4:
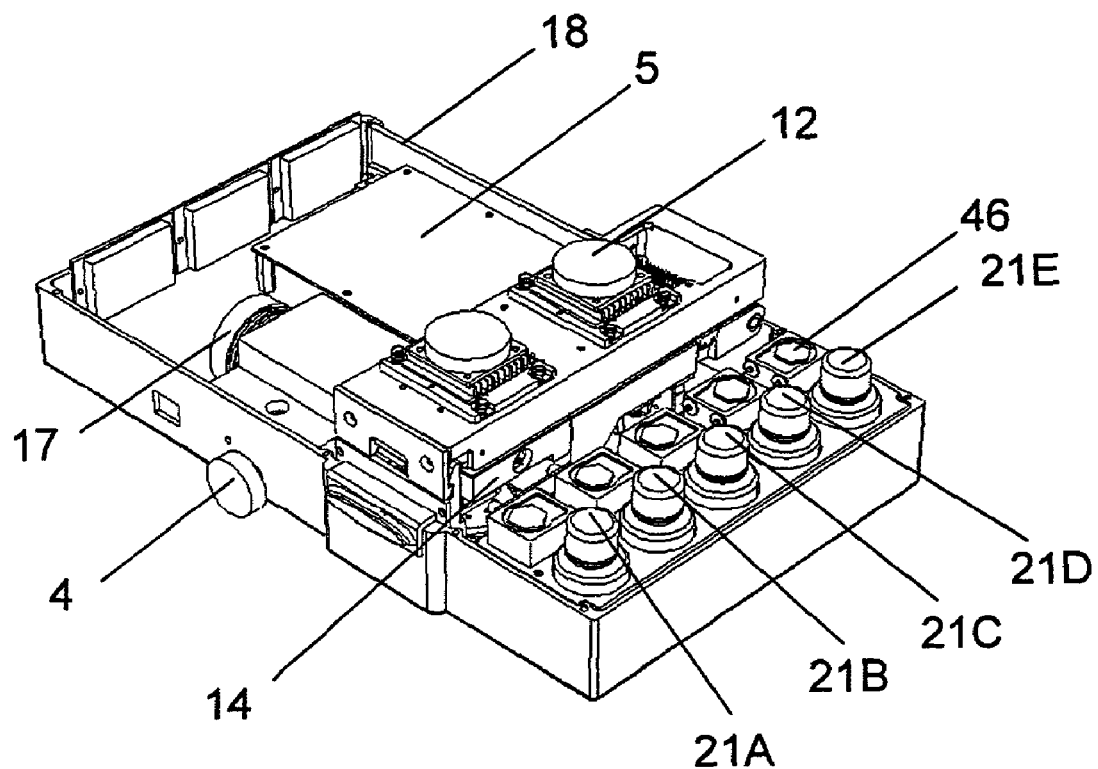
FIG. 4 is a an internal view of the integrated system showing various components thereof such as sample and reagent vials 21A–E, heating elements 12, CCD camera 17, laser 14, a series of pumps 46 for each reagent vial, and other features such as a focus adjustment knob 4 and area for electronic components 5.

FIG. 3 shows a perspective view of one design or style for the overall portable, integrated lab-on-a-chip system. A computer 20, preferably a portable notebook personal computer, includes conventional elements such as a keyboard, function keys, a monitor, and input devices, e.g., trackball, and mouse. Housing 18 serves to contain not only the preparation, reaction, and analysis platforms comprising the flow cell, but also additional equipment utilized in conjunction with computer 20 for operation of the system. For example, housing 18 may contain (FIG. 4) a power supply, waveform generator, laser, flow cell(s), CCD camera, and other electronics, fluidic systems, and reagents required for operation and control of the system.

Figure 5:
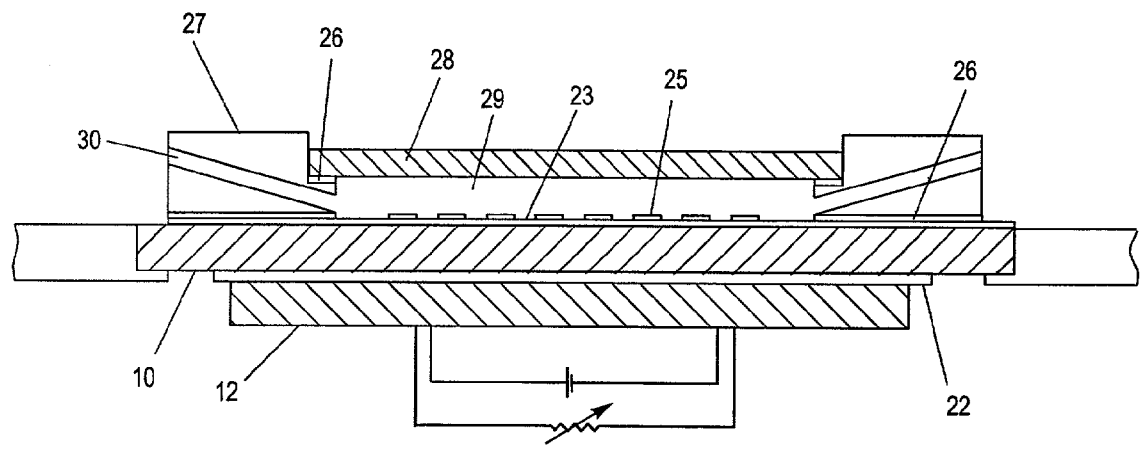
FIG. 5 is a cross-section diagram for a flow cell having a microchip grid. The flow cell in total comprises a microchip grid 23 on the inner bottom surface of the flow cell chamber 29. The flow cell is covered by a quartz window 28. The underside of the microchip substrate has attached thereto a heating element 12. The flow cell has at least two inlet ports 30.

As an example of a flow cell design, FIG. 5 shows a cross-section of such a cell. An electronically addressable microarray 23 is mounted onto substrate 10 containing a 1.0 inch square pin grid array (PGA) (068 PPGA, 400 Square Cavity, Spectrum Semiconductor Materials, San Jose, Calif.). Attached to the back side of the substrate 10 is a ceramic chip heater element 12 (Dawn 505, Dawn Electronics, Carson City, Nev.). The heating element 12 may be attached by any number of methods. In a preferred embodiment, the attachment may be achieved by placing a thermally conductive flexible adhesive 22 between the backside of the electronic microchip and the ceramic heater and then incubating at an appropriate temperature and time to fix the adhesive. Additionally, as is well understood in the art, these microchips are coated with a thin permeation layer 25 such as a hydrogel, agarose, a polymer of acrylamide, or a sol-gel matrix or the like. This permeation layer 25 protects the cells and molecules of interest (i.e., biomaterials) from the electrochemistry occurring at the electrode surface that would otherwise damage the biomaterials (or the ability to assay them) if they were exposed directly to the electrodes.

The microchip can be then attached to a molded or machined medical grade plastic flow cell 27 so that the electronic microarray 23 makes up the inner bottom surface of a well within the flow chamber. The flow cell 27 provides a compartment 29 for containing biological sample materials and buffers to be layered on top of the microchip. The flow cell may be further designed to have at least 2 to 4 ports 30 for sample delivery and extraction. The flow cell 27 may further be constructed so as to accept tubing for interfacing with exterior fluidic delivery and removal systems as well as desalting. Additionally, the flow cell compartment is covered and sealed by a fused quartz window or lid 28 for visual access to the microarray analysis sites or capture pads. This window 28 can comprise any thickness of quartz but generally is about 0.015 inches thick.

The window 28 may be attached to the flow cell and the flow cell to the chip by any number of methods of which a preferred method uses an ultraviolet (UV) curing adhesive 26 developed for optics assembly. Attachment of the flow cell to the chip may be either directly to a bare surface of the chip or to the permeation layer overlaying the microarray also using adhesive 26. Tubing is attached to the inlet and outlet ports using a variety of methods depending on the tubing size, fittings, and the tubing base material.

Figure 6:
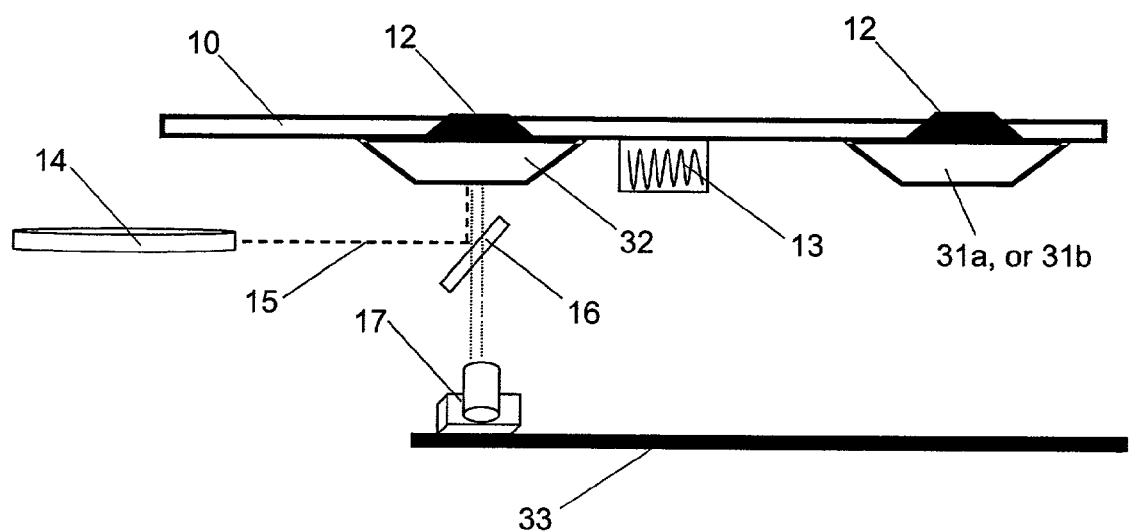
FIG. 6 is a schematic showing an alternative embodiment having two flow cells. In this embodiment, a first flow cell can comprise either a cell having an electronically addressable microchip 31a, or not having such a microchip 31b. In either case, flow cell 31a,b has attached thereto a heating element 12. In this embodiment, the second flow cell 32 has an electronically addressable microchip attached to a heating element 12. As with the preferred embodiment diagrammed in FIG. 2, the integrated system further includes a desalting column 13, laser 14 with light path 15, and a detector 17 positioned on a movable track 33 for positioning the detector for astronomy of either flow cell.

In an alternative embodiment, the integrated system may use two flow cells, one for sample preparation and the second for analysis. FIG. 6 shows in schematic form such an embodiment. The first flow chamber 31 is attached to a heating element 12 and may optionally have an electronically addressable microchip 31a or no such microchip 31b. In either format, i.e., with or without electronic microchip, the flow cell 31 is used to perform in a stepwise fashion cell separation and/or cell lysis, and clean-up and further preparation of molecules of interest recovered from the lysed cells. Further preparation of molecules of interest is contemplated to include any number of chemical reactions and steps as stated above such as isolating specific proteins of interest, isolating nucleic acids of interest such as by treatment with proteases to remove proteinaceous material from the nucleic acids, and amplification of nucleic acids of interest such as by PCR and SDA.

The second flow cell 32 is used for sample analysis. In a preferred embodiment both flow cells 31 and 32 are disposed on the same side of the support 10. However, these flow cells may be disposed in alternative arrangements, including a back-to-back or a stacked configuration. Additionally, these two flow cells may be connected via a hollow fiber in order to purify, desalt and introduce different buffers into the flow stream. Moreover, each flow cell may be designed to have independent temperature control elements as desired. As will be understood by one of skill in the art, each of the electronically addressable microchips within the flow cells, as well as the other electrically operated components, such as solenoid operated valves and pumps, are interconnected electronically with the computer 20 by cabling for all programming and control purposes as in the single flow cell arrangement.

FIG. 6 further shows illumination source 14 that emits a laser beam 15 and operates in the same fashion as described above. A camera with zoom lens 17 for astronomy of the electronic grids of the flow cells is also incorporated on a movable track 33 so that both the first and second flow cell electronic microarray grids can be viewed.

Figure 7:
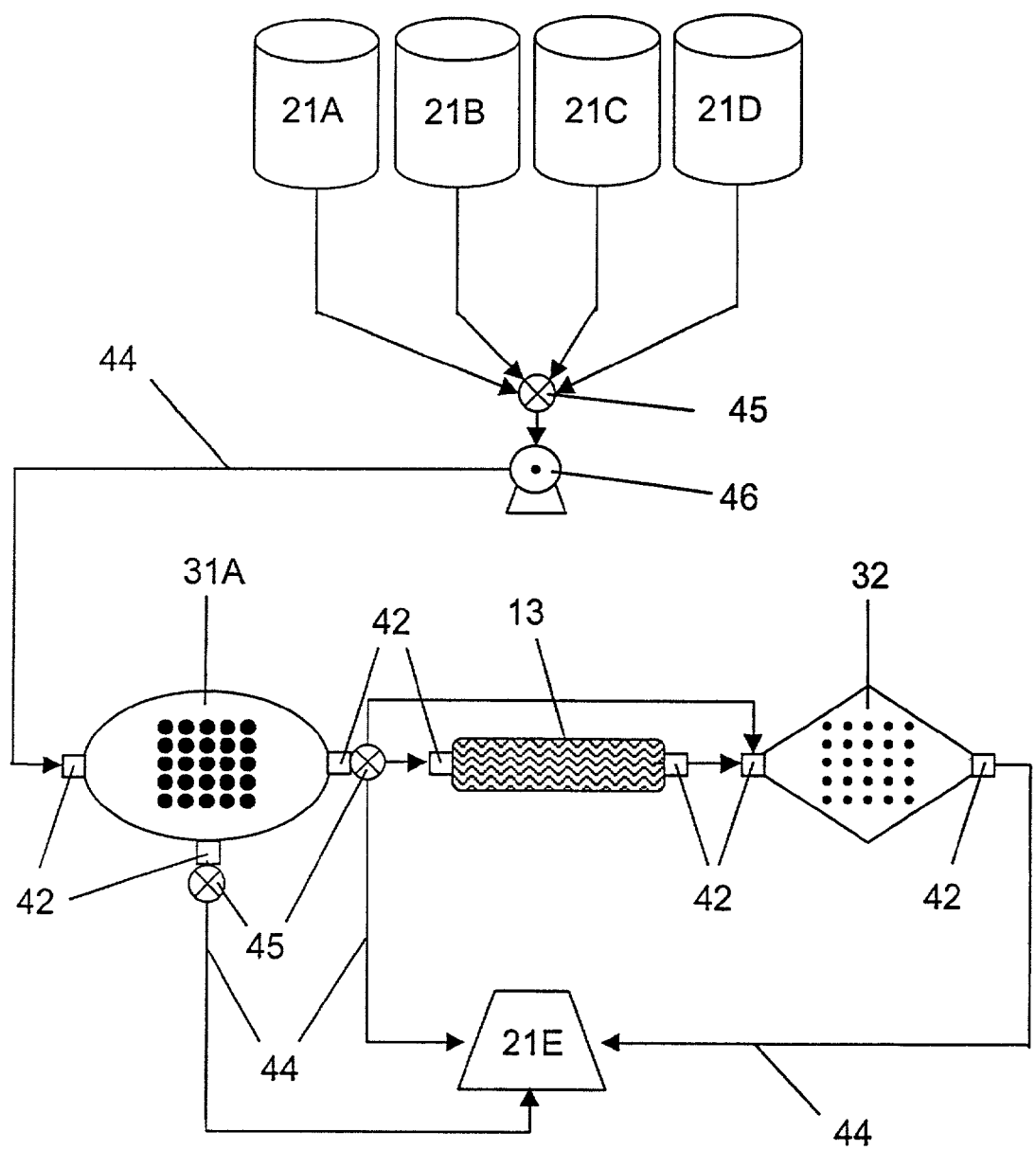
FIG. 7 is a schematic showing a two flow chamber embodiment wherein first 31a and second 32 flow cells are arranged adjacent to one another. Also depicted are flow systems for channeling buffers, reagents, and analytes through the flow cells and desalting column of the system.

FIG. 7 is a schematic of the alternate system showing support 10 including the flow cells for sample preparation 31a (shown as an electrode comprising flow cell) and analysis 32 (shown as a 25 electrode grid). Each of the flow cells preferably include a plurality of ports 42 connected to tubing or hollow fiber 44 leading to electrically operated 3-way valves 45. With respect to the preparation flow cell 31a, the cell is contemplated to possess at least two ports 42, optionally at least three ports, and in the preferred embodiment four ports. With respect to the analysis flow cell 32, this cell preferably has two ports. These ports 42 and their respective tubing 44 may be utilized for various functions at different times. For example, at one time a port may be considered an input port, whereas at another time, it may comprise an output port, based on the directionality of the flow into or out of the flow cells 31 and 32 as directed by the setting of the 3-way valves 45 and directionality of pump 46. Fluids in the chambers may be mixed by "pushing" and "pulling" of the liquids in various sequences through the ports. Such mixing may be advantageous, for example, during an amplification procedure.

FIG. 7 further depicts other components of the self-contained system. In one embodiment, receptacles 21a–e provide for carrying samples and reagents such as for washing, amplification, hybridization, and waste. In another embodiment, the support 10 has attached thereto a miniature desalting column or a hollow fiber ion-exchange unit 13 for desalting small sample volumes. Often, there is a need to perform a desalting step to lower the ionic strength of the sample prior to attempting to electronically address amplified nucleic acids to specific capture pads of the microarray. This is because reagents used in amplification steps have an ionic strength that interferes with the migration of molecules of interest under the electronic addressing protocols. Once the amplified sample has been desalted it can be directed to the flow cell 32 for analysis on the microarray.

Whether using a single or multiple flow cell integrated system of the invention, cell separation is achieved by a dielectrophoresis technique. In such method, polarizeable particles (e.g., eukaryotic and prokaryotic cells) including those with no net charge are subject to a "dielectrophoretic" force of a non-uniform electrical field. As long as the effective polarizability of the particles is different from that of the surrounding medium, the cells will remain subject to the dielectric force. The direction of migration of different cell types is determined by: (1) surface charges of the cell walls or membranes of the cell bilipid membranes, (2) the conductivity and permitivity of such cell membranes and walls, and (3) the morphologies and structural architectures of the cells. Dielectrophoresis as practiced in the current invention has been used to selectively separate from mixed cell populations (e.g., blood cells) several types of bacteria including *Escherichia coli, Salmonella typhimurium, Micrococcus lysodeikticus* and *Staphylococcus epidermidis* as well as cancer cells such as cultured cervical carcinoma cells.

Figure 8:
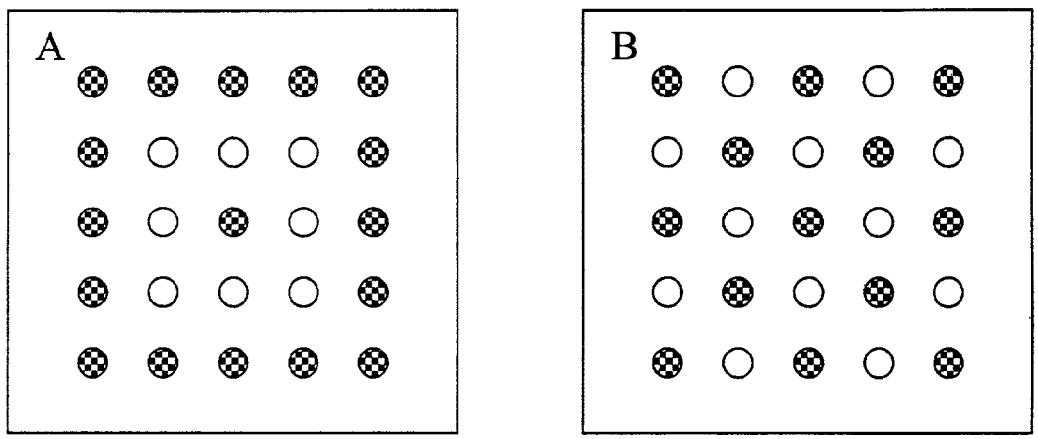
FIG. 8 shows bias pattern formats that can be used to create a pattern of dielectric force for separation of eukaryotic or prokaryotic cells. In (A) is depicted a square-wall dielectric force pattern. In (B) is depicted a checkerboard force pattern.
Figure 9:
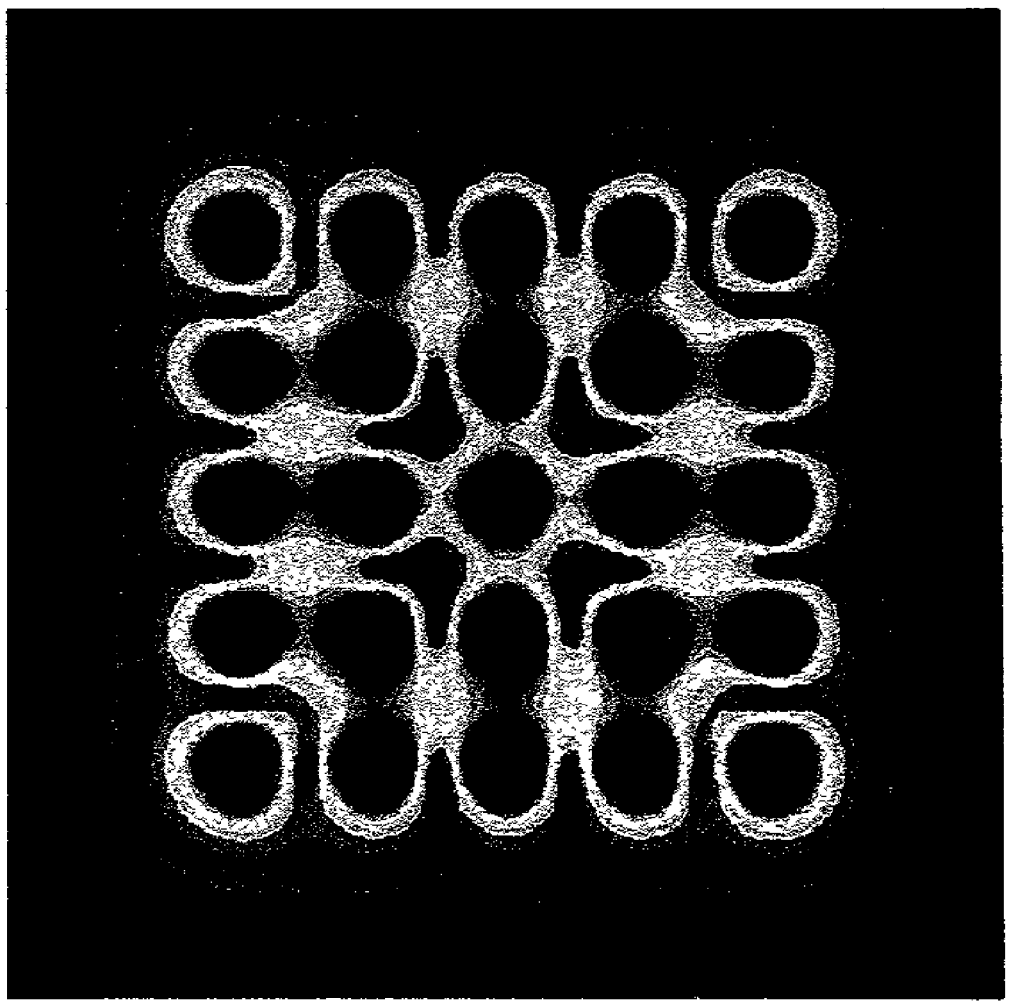
FIGS. 9 and 10 show two computer representations of dielectric field distributions corresponding to either a square-wall or a checkerboard force pattern respectively.
Figure 10:
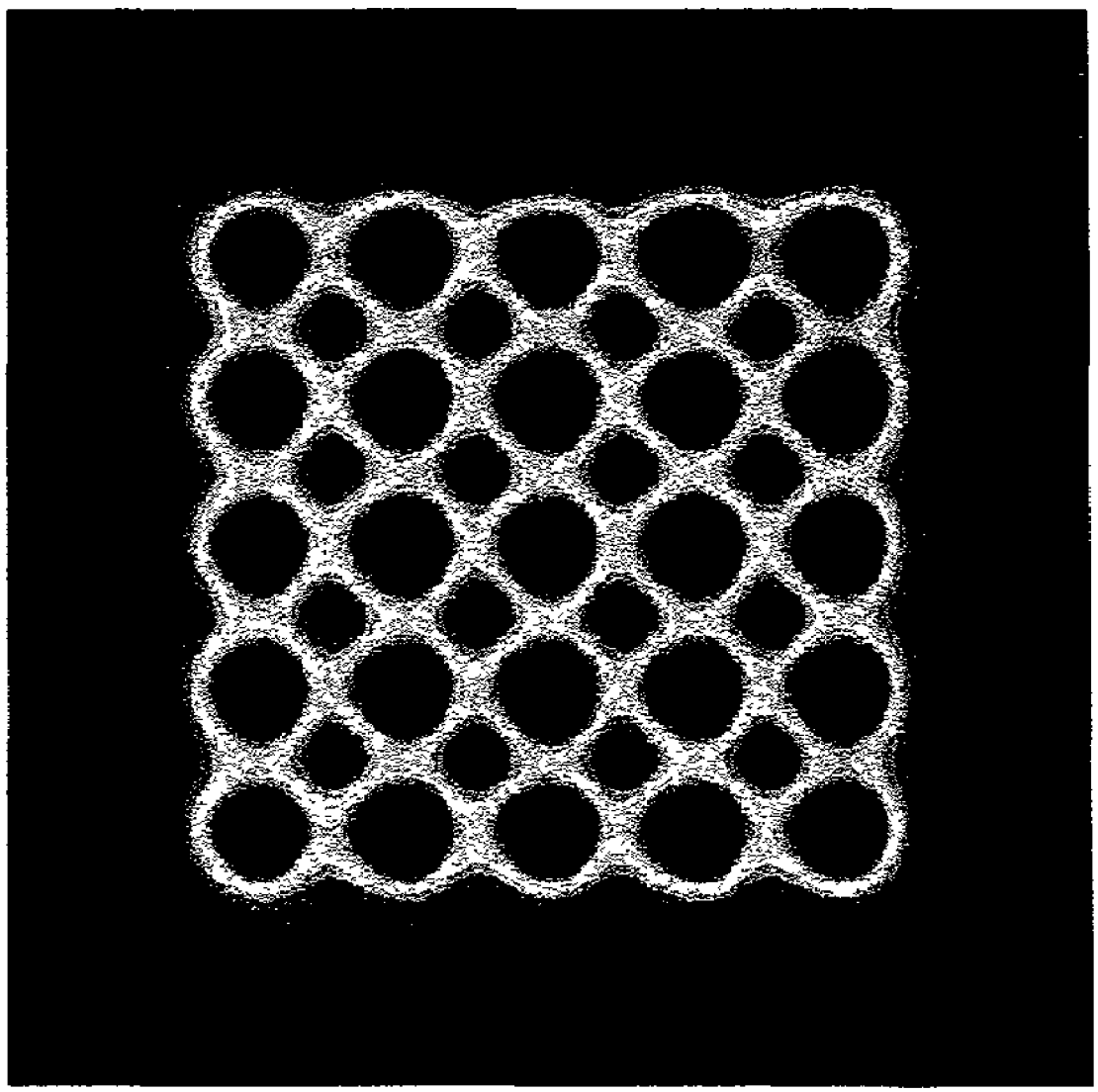

In a preferred embodiment, a flow cell useful for separating cells as practiced in this invention may be designed to include an electronically addressable microchip having at least 100 individually addressable microelectrodes capable of being biased individually so that a dielectric force pattern may be generated across the microchip electronic grid. For example, FIG. 8 shows two such force patterns. In FIG. 8A is a square-wall pattern while 8B shows a checkerboard pattern. Each of these patterns provide a unique strong and weak ionic field strength pattern that provides dielectric force sufficient to separate different cell types. The force pattern is further depicted in computer generated field patterns shown in FIGS. 9 and 10 for square-wall and checkerboard respectively.

Additionally, the electrodes of the microarray in the flow cell(s) may be biased either all together as a single array for carrying out cell separation, lysis, and analysis, or may be programmed to form subarrays in any number of patterns for carrying out the separation, lysis, and analysis steps. In other words, one subset may be biased to separate cells, another set may be biased to cause cell lysis, and yet another set may be used for analysis.

Figure 11:
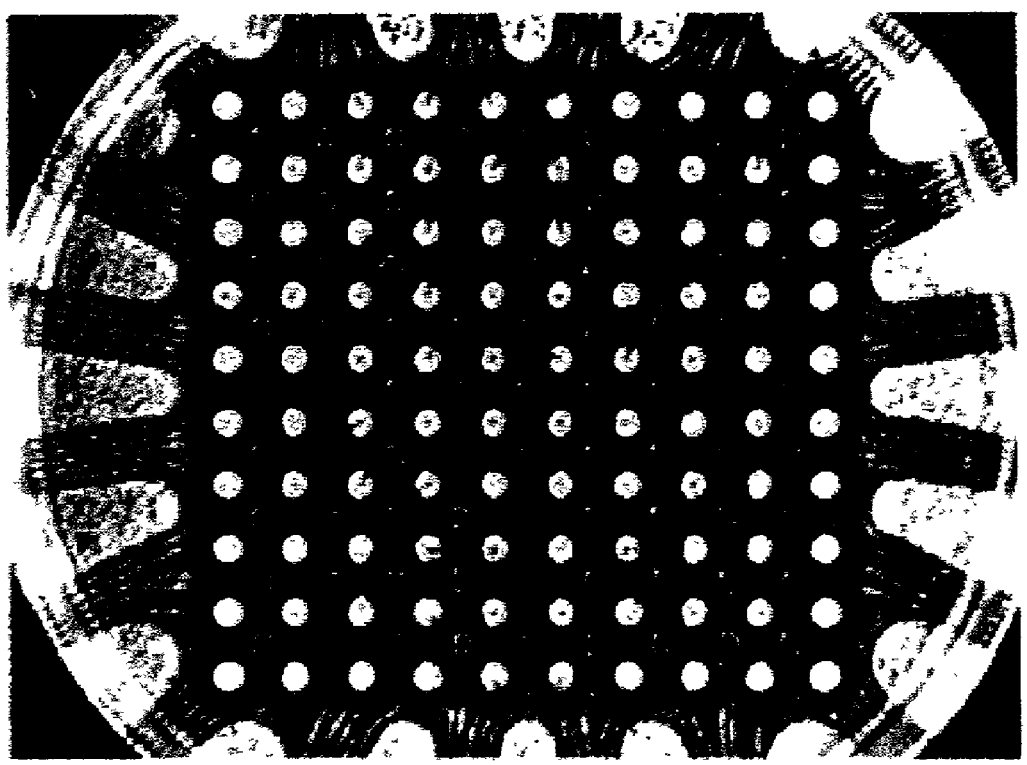
FIG. 11 shows an electronically addressable microarray in a flow cell during cell separation. The figure specifically depicts a bacterial species being separated from whole blood using a checkerboard dielectric force pattern applied to the electrode of the flow chamber. The bacteria are the light colored concentrations at the field charge maximums directly above the electrodes of the array while the blood cells are in between the electrodes at the field charge minimum areas.

In an example of cell separation, FIG. 11 shows the separation of *Micrococcus lysodeikticus* from whole blood. The bacteria are concentrated above the electrodes while the undesired blood cells, both red and white cells, are dark areas in between the electrodes. The cells were made to separate using a protocol of biasing comprising a sinusoidal signal of 10 V peak-to-peak at 10 kHz. Although this signal value was used in this instance, generally cell separation can be carried out using sinusoidal signals wherein the Volts are between 2 and 20 peak-to-peak while frequencies are between 5 and 50 kHz.

Figure 14:
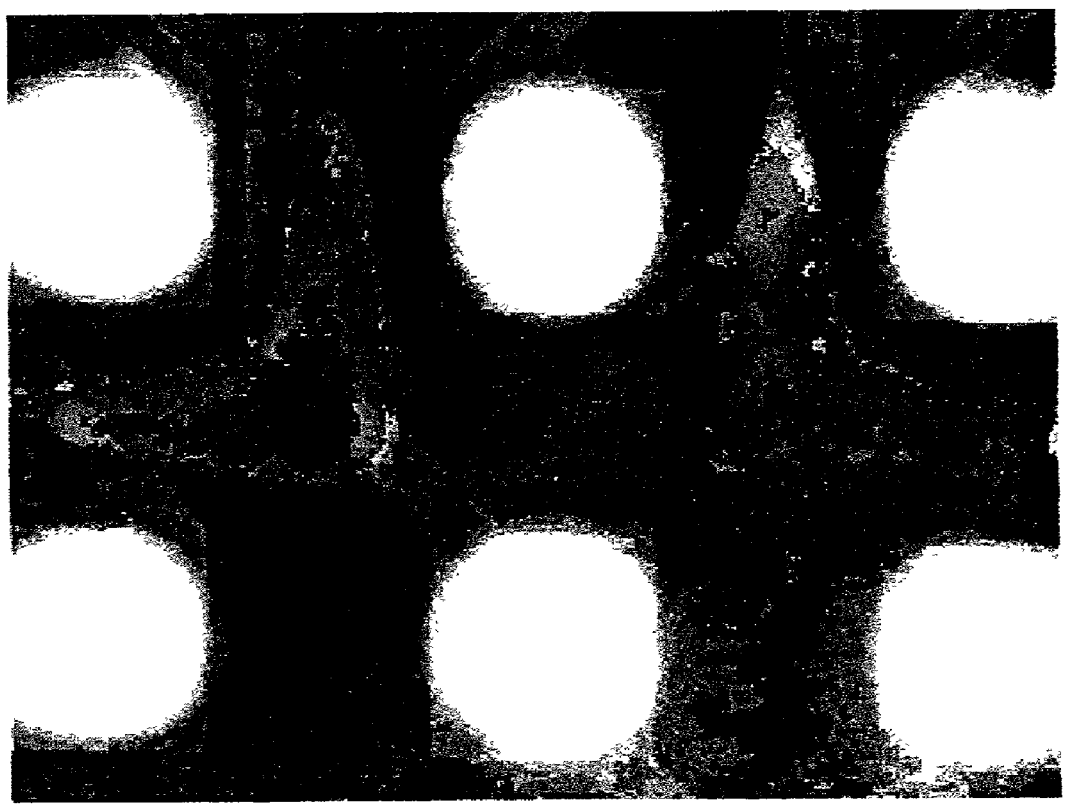
FIGS. 14–17 show a series of photographs where bacteria cells are separated from blood cells using either a square-wall or checkerboard dielectric field pattern.
Figure 15:
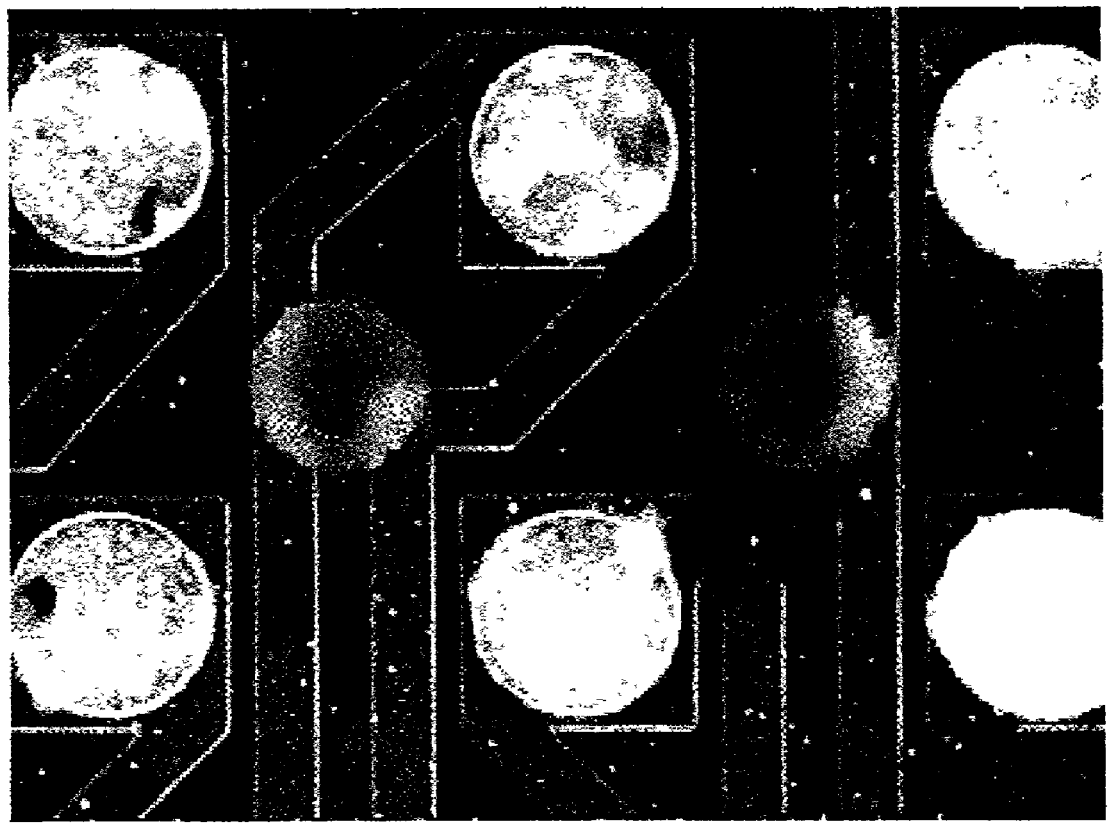
Figure 16:
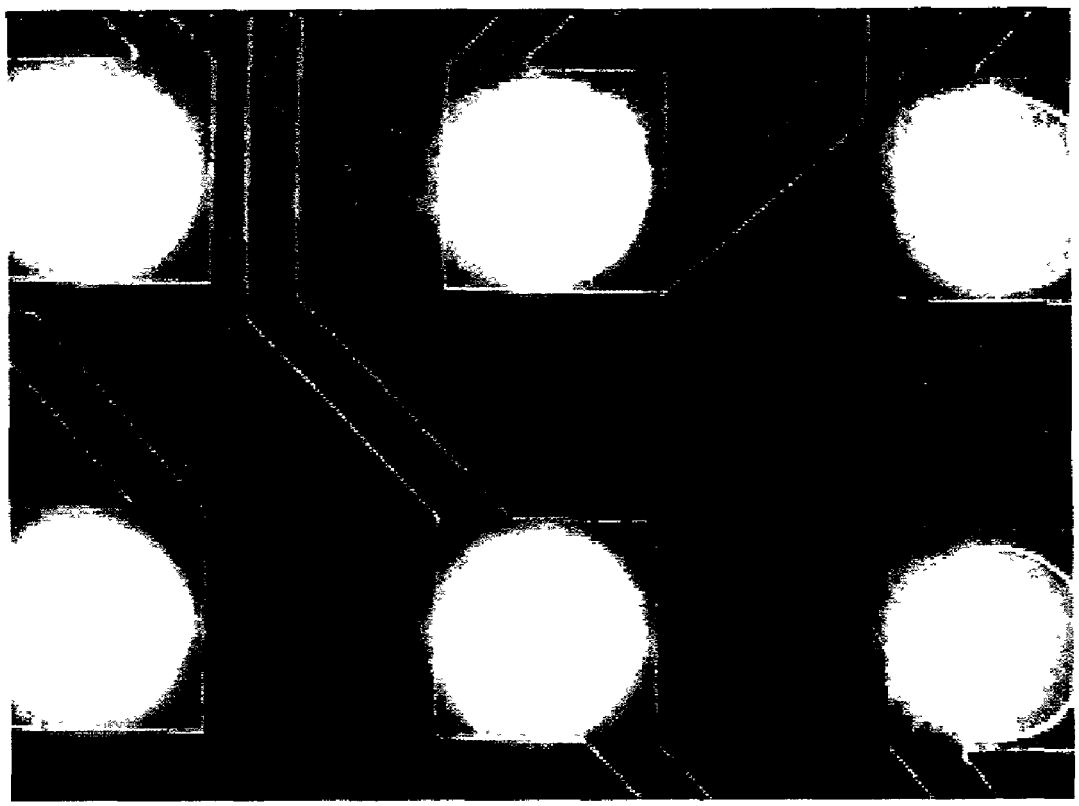
Figure 17:
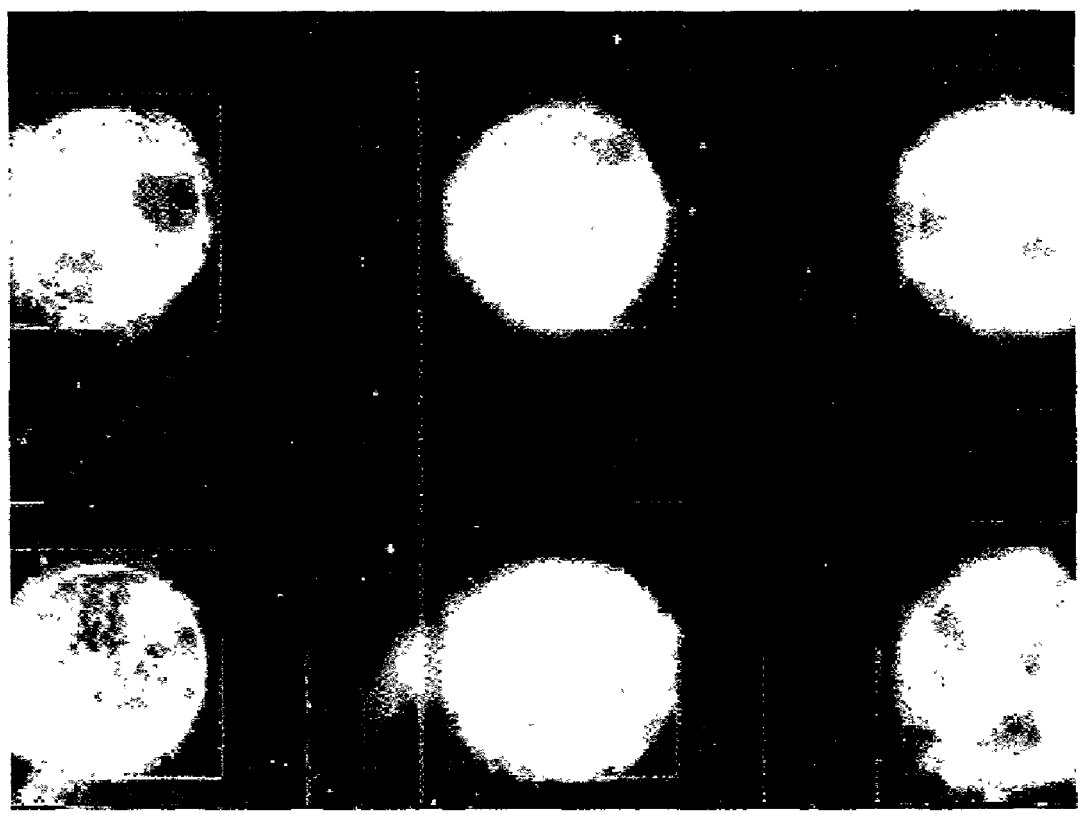

Undesired cells are washed from the flow chamber while retaining the cells of interest. This is accomplished by maintaining an attractive bias for the cells of interest and creating a flow of wash buffer through the flow chamber. Once the cells of interest are isolated in the flow chamber they may be treated in any number of ways for further processing. In one embodiment, the cells are lysed by applying high voltage pulses of up to 450 volts with a pulse width between 10 µs and 50 µs as described in J. Cheng, et al., "Preparation and hybridization analysis of DNA/RNA from *E. coli* on microfabricated bioelectronic chips," *Nature Biotechnol.*, 16, pp. 541–546, 1998. In another example, *E. coli* cells were separated from blood cells as shown in FIGS. 14–17. In FIG. 14 a square-wall dielectric force pattern was used while in FIG. 15, a checkerboard pattern was used. As an example, the separation for the checkerboard pattern used a bias format of a sinusoidal signal of 10 V peak-to-peak at 10 kHz. FIGS. 16 and 17 show how cleanly the bacterial cells were isolated following washing of the square-wall and checkerboard patterned separation.

Figure 12:
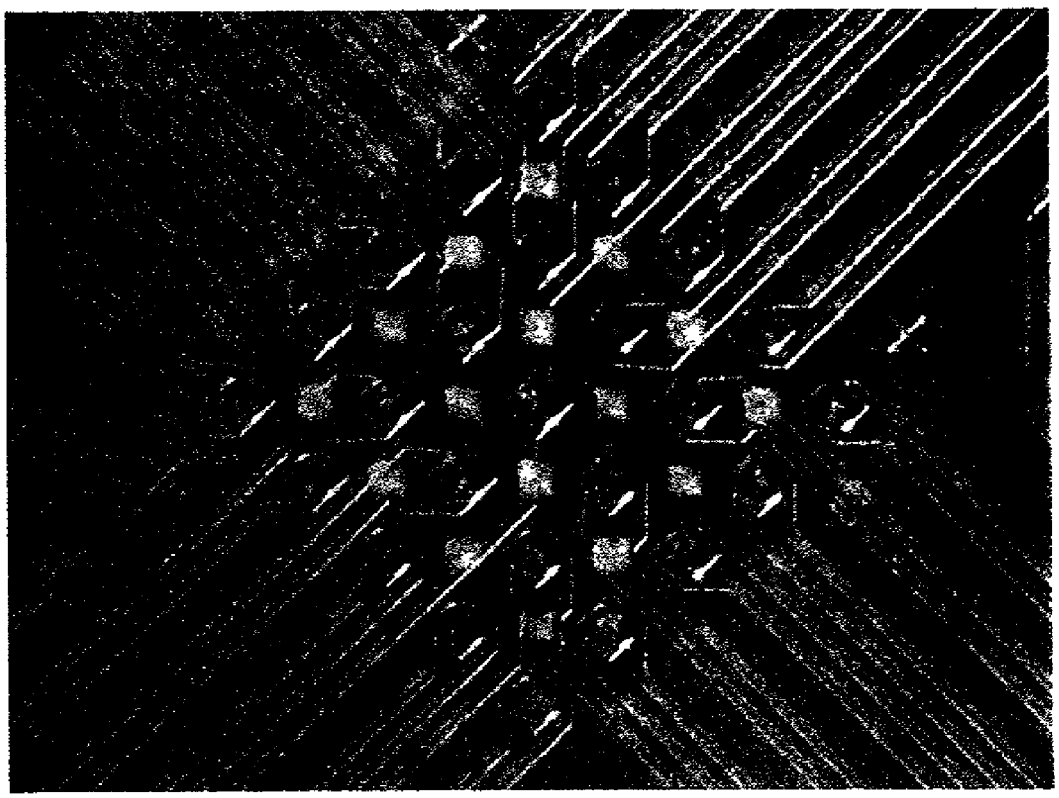
FIGS. 12, 13A and 13B show eukaryotic cells (cultured HeLa cells) being separated from blood cells (FIG. 12) and after washing (FIG. 13A) and staining with propidium iodide (FIG. 13B). The mixture of the normal human white and red blood cells was pushed to the space between the electrodes where the field was minimum, as reflected by the relatively brighter spots within the field minima in FIG. 12.
Figure 13A:
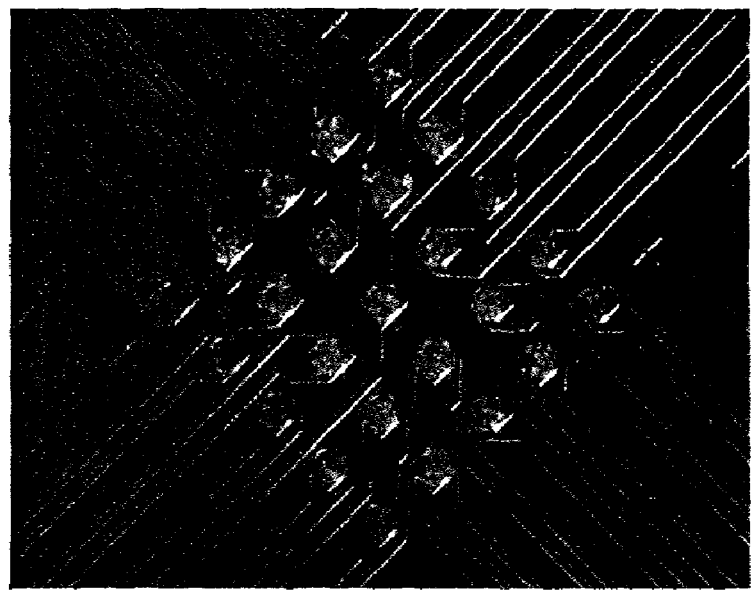
Figure 13B:
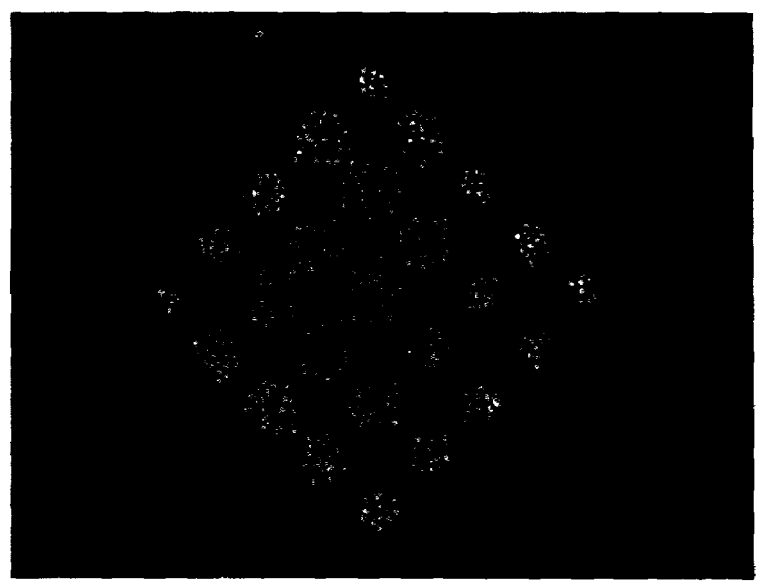

In another example, mammalian cells are separated on the electronic grid of the flow chamber. FIGS. 12, 13A and 13B show separation of cervical carcinoma cells. FIG. 12 shows initial separation wherein the cells move onto the electrodes of the grid where the field is at a maximum by subjecting the cells to a positive dielectrophoretic force. The mixture of the normal human white and red blood cells mixed with the carcinoma cells are pushed to the space between the electrodes where the field was minimum, as reflected by the relatively brighter spots within the field minima. After washing, the carcinoma cells were retained by the electrodes (FIG. 13A) whereas all of the normal blood cells were washed out. FIG. 13B shows the cells after staining with propidium iodide. As an example, the mammalian cells could be separated using the checkerboard format and applying a sinusoidal signal of 6 V peak-to-peak at 30 kHz for 3 minutes. J. Cheng, et al., "Isolation of Cultured Cervical Carcinoma Cells Mixed With Peripheral Blood Cells on a Bioelectronic Chip," *Anal. Chem.* v.70, pp 2321–26, 1998.

Figure 18:
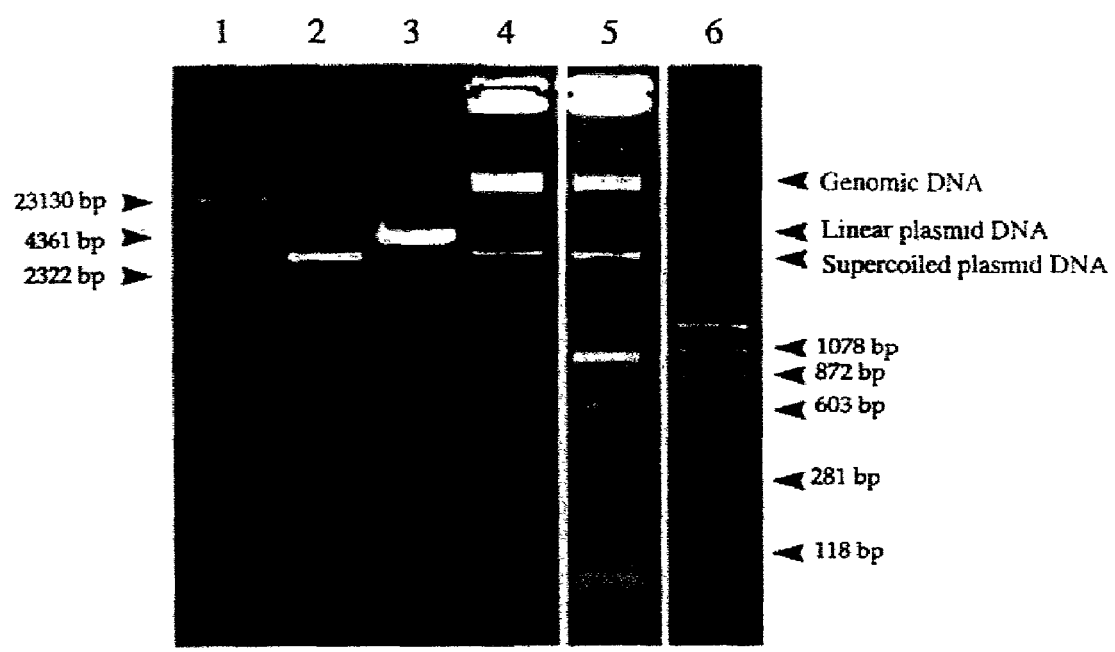
FIG. 18 is a photo of a PAGE showing analysis of nucleic acids released from bacteria by electronic lysis. Lanes 1 and 6 are markers, lanes 4 and 5 are whole bacteria DNA with and without Rnase treatment respectively, and lanes 2 and 3 are supercoiled and linear plasmid pCR2.1 DNA released from the bacteria.

Following lysis, both cellular proteins and nucleic acids may be retained for analysis. An example showing that nucleic acid may be retained from lysed cells is provided in FIG. 18. There, *E. coli* DNA is run on a PAGE gel showing both chromosomal and plasmid DNA is retained.

Where nucleic acids are desired for analysis, further clean-up and purification may include treatment with proteases such as with Proteinase K. After such treatment, the lysate may either be analysed immediately, or amplified then analysed. If the alternate embodiment is used, the sample may be further treated in the flow chamber or may be exported to the second chamber for such protease treatment, amplification and analysis. Generally, a protease treatment may be carried out in an appropriate buffer at 60° C. for 15 min. Temperature control may be achieved by use of the ceramic heater element attached to the back of the microchip. Inactivation of proteinase K may be achieved by heating the sample at 95° C. for 2 min. Overall, the cell separation, lysis, and protease treatment process can take between 15–25 minutes.

Where proteins are desired, nucleic acids may be removed by treating the sample with restriction enzymes and nucleases. The proteins may further be treated with various enzymes and partial protease treatments to release specific proteins of interest from cell membranes and other cellular components. Following the above sample processing steps additional processing may be carried out including amplification (e.g., by PCR and SDA) and labeling with radioisotopic or fluorescent markers.

In an example of chemical reaction stage processing, specific nucleic acid sequences, (i.e., the invA and spa Q genes of *Salmonella enterica*) were amplified using SDA. SDA is preferred in this portable system as the amplification may be performed under isothermal conditions at between 50° C. and 60° C. thereby eliminating high temperature denaturation cycles associated with PCR. However, in one embodiment, the portable system is capable of performing PCR amplification as the flow chamber is equipped with the aforementioned heating element that has the capability of achieving repetitive high temperature cycling.

Figure 19:
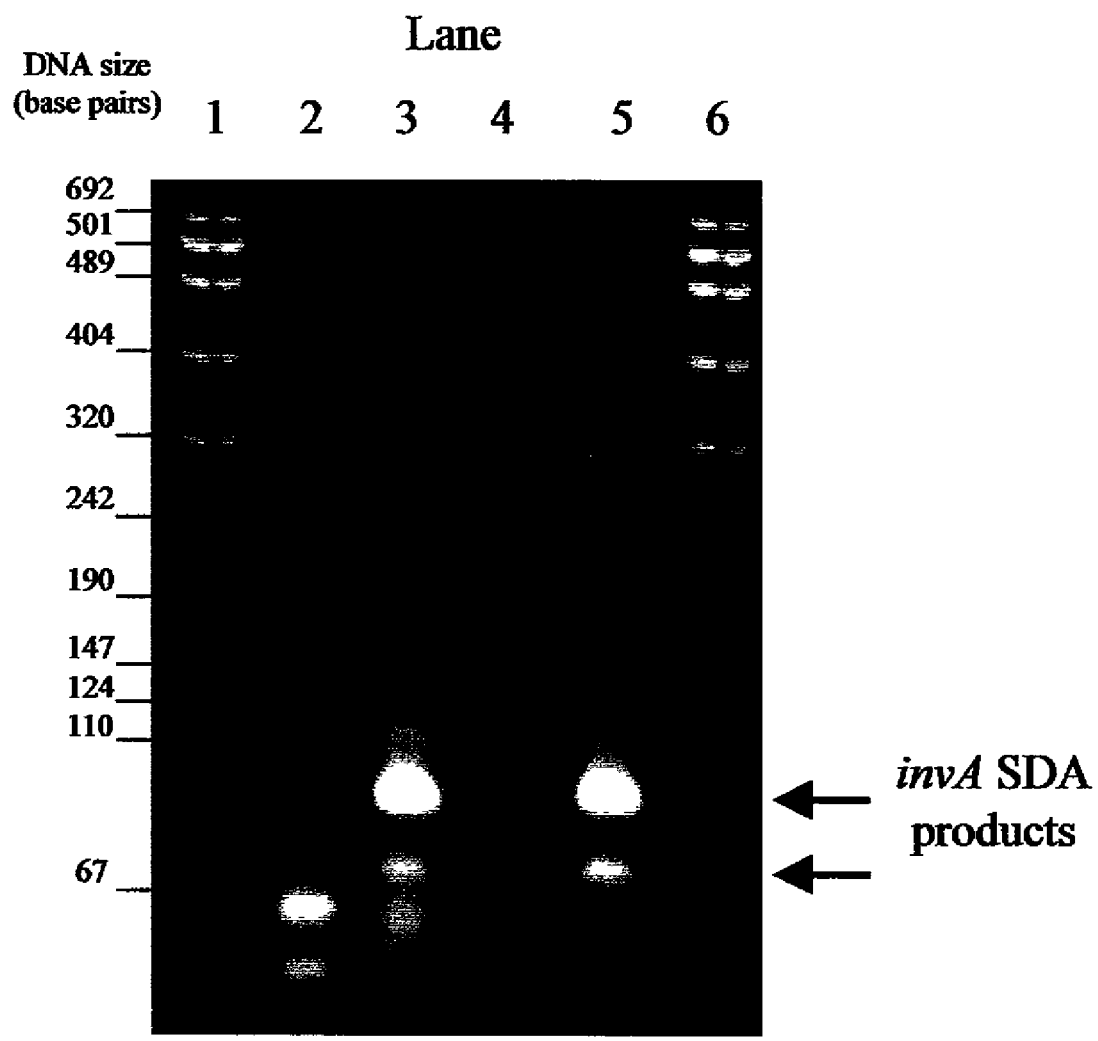
FIGS. 19 and 20 are PAGE photos showing amplification of two S. enterica genes spa Q and inv A, by SDA in the flow cell of the invention.
Figure 20:
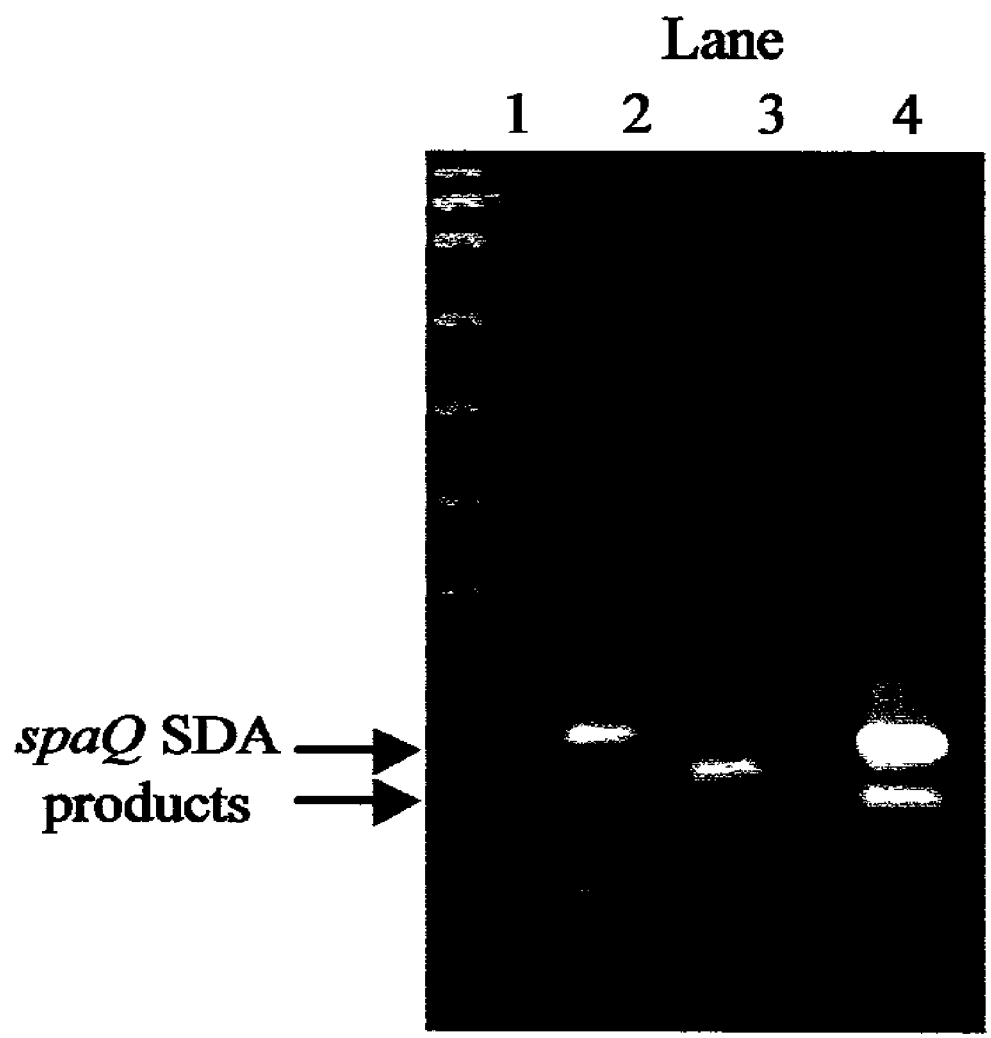

As shown in FIGS. 19 and 20 SDA can be effectively performed in the device with a product yield comparable to the positive control performed in a conventional reaction tube. In this example in a volume of 50 μl, *Salmonella enterica* and blood cells were mixed and injected into the flow cell containing a 10,000 site electrode array. The bacterial cells were separated from the blood cells by dielectrophoresis using a biasing protocol of 10V peak-to-peak signal having a sinusoidal wave form with frequency of between 10 and 15 kHz using the checkerboard pattern. The cell mixture was pumped into the flow cell at a rate of 31 μl per minute until the flow chamber was filled, then the flow rate was adjusted to 12.4 μl/min until the total 50 μl volume was passed through the chamber. The cells were retained above the electrodes by influence of the positive dielectrophoretic force established by the protocol. The flow cell was then washed with water to remove cells not retained by the positive bias by pumping buffer in a reverse direction at a rate of 114 μl/min for 10 minutes. The fluid content of the flow cell was then exchanged with a solution of SDA reagents for amplifying either the spa Q or inv A gene sequences.

The total nucleic acid from the bacteria cells was isolated by first lysing the cells by energizing the electrodes with pulsed direct current at 200 V having a square wave form af 10 ms duration and a total of 40 separate pulses. (Alternatively, the cells can be lysed by heating the chamber to 95° C. for five minutes). A concentrated SDA reagent and buffer stock mix was introduced into the flow cell and mixed with the denatured target nucleic acid to give the following final concentrations of SDA reaction components: 500 nM amplification primers, 50 nM 'bumper' primers, 9.5 mM magnesium acetate, 35 mM potassium phosphate buffer pH 7.6, 80 μg/ml bovine serum albumin, and 1.4 mM each of dATP, dGTP, TTP, and alpha-thiolated dCTP. The amplification primers were designed to amplify 81 base pairs of the invA or spa Q gene and comprised the following nucleic acid sequences:

spa Q Seq. Id. No. 1 5'-accgcatcgaatgcatgtctcgggtc-ctggtagggttattc-3'
spa Q Seq. Id. No. 2 5'-cgattccgctccagacttctcgggaaca-cacgccaagta-3'
inv A Seq. Id. No. 3 5'-accgcatcgaatgcat-gtctcgggtttcaacgtttcctgcg-3'
inv A Seq. Id. No. 4 5'-cgattccgctccagacttctcgggatc-gataatgccagacg-3'

Bumper primers comprised the following sequences:
spa Q Seq. Id. No. 5 5'-gcaacgattatcggc-3'
spa Q Seq. Id. No. 6 5'-ccagacagtaaaaac-3'
invA Seq. Id. No. 7 5'-ttgacagaatcctca-3'
inv A Seq. Id. No. 8 5'-taagacggctggta-3'

The released nucleic acid was then denatured by heating the chamber to 90° C. for five minutes. The chamber was then brought to 60° C. and 10 μl of SDA reagent buffer containing enzymes was introduced into the chamber to initiate amplification (i.e., 40 units of BsoB1 restriction endonuclease and 16 units of exo-Bst DNA polymerase).

In the system of the invention, amplification using SDA may be carried out for between 25 and 35 minutes. In the present example, after 30 minutes of reaction a 5 μl aliquot of the reaction volume was removed for PAGE analysis (FIGS. 19 and 20).

The third stage of sample handling comprising detection of the molecules of interest is preferably carried out for proteins and nucleic acids of interest. Such detection can use various forms of hybridization to probes previously attached to the microarray. For example, nucleic acids (e.g., RNA, DNA, and pNA) may be used for binding sample-derived nucleic acid analyte (e.g., amplified or unamplified target nucleic acids) by hybridization. Proteins may also be made to bind to capture molecules (i.e., protein-ligand binding interactions) attached to the array. Such capture molecules may comprise proteins or other molecules and the binding interaction can comprise such interactions as antigen-antibody, enzyme-substrate, and receptor-ligand binding.

With respect to nucleic acids, target species, whether amplified or not, are electronically addressed to specified capture pads of the microarray of either the single (or the secondary) flow chamber for capture by oligonucleotide probes that are anchored thereto. Preferably, the electrode array of the flow cell, (i.e., flow cell 11, 31*a* or 32 depending upon the embodiment and protocol used) has at least 25 individually-addressable electrodes coated with a permeation layer (e.g. for example, an acrylamide-based hydrogel). The target nucleic acid is biased using a positive sinusoidal signal generated using a function generator/arbitrary wave form generator (33120A, Hewlett Packard, Santa Clara, Calif.). The capture probe-target hybrids are then detected using fluorophore-labeled reporter probes and the CCD-based optical imaging system employed for the portable instrument shown in FIG. 2. Detection with this arrangement takes approximately 5 min to accomplish.

Figure 21:
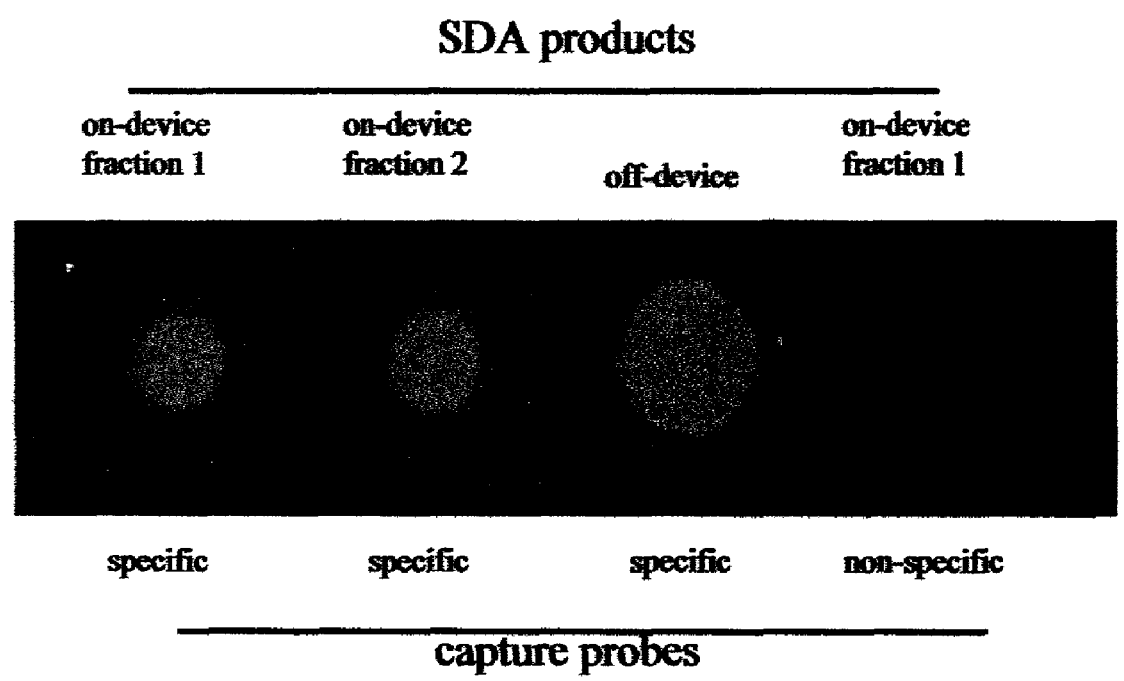
FIG. 21 is a photo showing hybridization results for spa Q gene wherein two electrode pads equipped with specific probe for spa Q gene were tested for hybridization in duplicate, a third pad specific for the gene was hybridized with amplified material from a positive tube reaction, and a fourth pad which was equipped with a nonspecific probe was tested for hybridization to amplification product produced in the flow cell.

Continuing with the above example, the amplification products of the spa Q and inv A genes were available for capture and analysis. Prior to capture, the SDA reaction solution and amplification products were passed through a desalting column in a volume of about 75 ul followed by exchanging the buffer with a 50 mM Histidine buffer. The amplification products were then addressed to specific pads of the electrodes which contained gene specific probes attached to the permeation layer overlaying the electrodes. This was followed by washing the chamber with 200 mM NaCl, 10 mM Tris pH 8.0, 1 mMEDTA, followed in turn by introduction of a bodipy 630-labeled probe oligonucleotide specific for the amplification product at a concentration of 0.5 µM in 200 mM NaCl, 10 mM Tris pH 8.0, 1 mM EDTA, and 100 ug/ml Calf Thymus DNA. The reporter probe solution was left in the assay cell for 10 minutes then washed with 7–800 µl of 50 mM Histidine buffer. The chamber was then visualized using a 630 nM helium-neon laser and a computer controlled CCD camera. FIG. 21 shows results of binding of the spa Q gene amplification product to individual pads of the electrode in the flow chamber. The binding shows that the amplification product produced in the flow cell annealed to the capture pads (fraction 1 and 2) satisfactorily in comparison to annealing of amplification product produced as a control in a reaction tube and then introduced into the flow cell chamber after the fractions 1 and 2 had been addressed. The level of binding for the control amplified product is higher due to the higher level of amplification obtained in the control reaction. We note that very little nonspecific binding of amplified product from the flow cell reaction bound to a capture site having a nonspecific capture probe.

Figure 22:
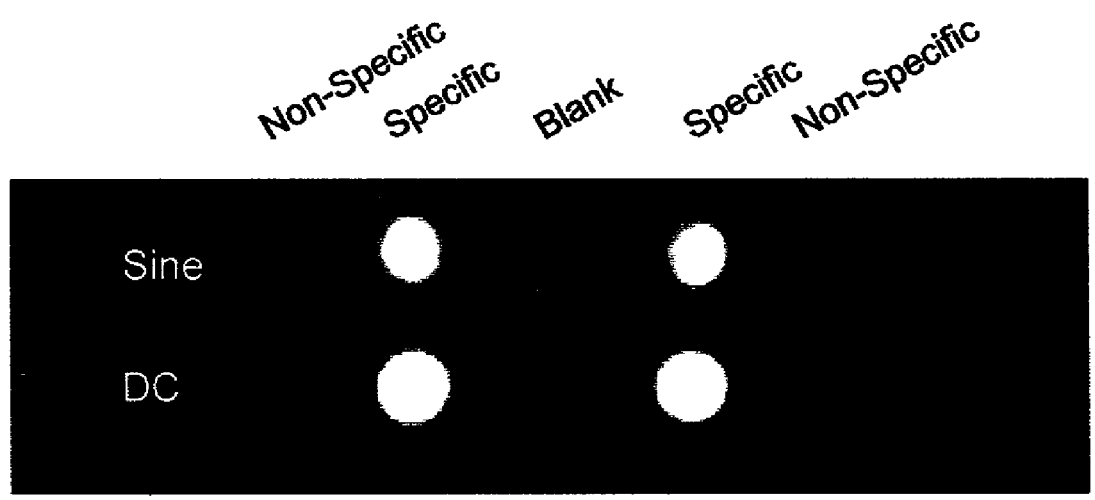
FIG. 22 is a photo showing amplified spa Q gene products addressed to capture sites of electrodes of the microarray using two different biasing conditions. In the top row is duplicate addressing to pads having capture probes specific for spa Q sequence (lanes 3 and 4) while lanes 1 and 5 have nonspecific probes. In the top row, a sinusoidal wave AC format was used while in the bottom row a direct current (DC) format was used. The results indicate that using a DC format is slightly superior to an AC format in transporting nucleic acids to the electrodes as the DC protocol bound a higher degree of amplicon.

In FIG. 22, the amplified SDA products for the spa Q gene were also addressed to specific pads on the microarray using two alternate biasing formats. In one biasing protocol, the amplicons were addressed using a sinusoidally based AC format of 3.5 V peak-to-peak at 1 kHz. This protocol also used a DC offset voltage of +2.3 V for 5 minutes. In the other protocol, a direct current (DC) format was used comprising +2.5 V for 2 minutes. As can be seen, the DC protocol is able to transport the molecules of interest to the capture sites with greater efficiency as the DC biased pads exhibit a greater binding signal. This result further shows the versatility of the system in that processing of sample materials (cells and molecules) may be manipulated in a wide range of adjustments that is possible using this electronic-based lab-on-a-chip system. For example, the use of an AC format though shown in the above example as providing less transport mobility to the specific sequence, can be performed where the voltage range is between 2.0 and 5.0 peak-to-peak, the frequency range is between 1 and 10 kHz, and the DC offset is in a range of 1–5 volts). This versatility of ranges provides for transport of molecules under variable buffer conditions.

Visual detection of amplification reaction products by probe hybridization may be performed by directing a battery operated diode laser having at least the capability of generating approximately 2 mWatts of laser power with an emission wavelength of 635 nm. The laser is used to excite fluorescent dye-label reporter probe (such as BODIPY-630). The wavelength of the emission filter is 670 nm. The dichromatic mirror has a wavelength cutoff at 645 nm. Alternatively, a direct electrochemical voltammetric detection system may also be used instead of light based detection as is understood by those skilled in the art.

Although the foregoing invention has been described in some detail by way of illustration and example for purposes of clarity and understanding, it will be readily apparent to those of ordinary skill in the art in light of the teachings of this invention that certain changes and modifications may be made thereto without departing from the spirit or scope of the appended claims.

What is claimed is:

1. An integrated system for the analysis of eukaroytic and/or prokaryotic cells in a biological sample comprising:
    an electronic system for cell separation, cell lysis, sample preparation, and sample analysis further comprising a flow cell, an input port coupled to the flow cell, an output port coupled to the flow cell, a plurality of individually addressable electrodes positioned within the flow cell and coupled to a power source configured to electronically disrupt cell membranes within the sample, and an array of probes coupled to the electrodes and adapted to bind to predetermined components within the sample for analysis of the components, and a heating element coupled to the flow cell, wherein the flow cell is adapted to receive the sample via the input;
    a detector operatively positioned to detect the molecules bound to the probes by a detectable signal;
    a power source coupled to the flow cell; and
    a portable housing configured to contain the electronic system, the detector, and the power source.

2. The system of claim 1, further comprising an illumination source operatively positioned to direct radiation to the probes.

3. The system of claim 2, wherein the illumination source is a laser, and the system further comprises a beam splitter.

4. The system of claim 1, further comprising a desalting column coupled to the flow cell, the desalting column configured to introduce a buffer into the flow cell.

5. The system of claim 1, wherein the electronic system further comprises a permeation layer overlaying the electrodes.

6. The system of claim 5, wherein the probes are attached to the permeation layer.

7. The system of claim 1, wherein the electrodes are addressable to form a square-wall dielectric force pattern.

8. The system of claim 1, wherein the electrodes are addressable to form a checkerboard dielectric force pattern.

9. The system of claim 1, further comprising a wave form generator coupled to the electrodes.

10. The system of claim 1, further comprising a computer coupled to the portable housing and located outside of the portable housing.

11. A method for performing an analysis of a biological sample having desired cells and undesired cells using an integrated portable system comprising a flow cell, a plurality of individually addressable electrodes positioned within the flow cell, and a portable housing containing the flow cell, the method comprising:
    introducing the sample into the flow cell via an input port coupled to the flow cell;
    creating a dielectric force pattern by individually biasing the electrodes positioned within the flow cell;
    subjecting the sample to the dielectric force pattern to separate the undesired cells from the desired cells in the sample;
    isolating the desired cells by maintaining an attractive bias for the desired cells and introducing a flow of wash buffer through the flow cell via the input port to eliminate the undesired cells, wherein the undesired cells are removed from the flow cell via an output port coupled to the flow cell;
    lysing the desired cells by applying an electric force within the flow cell to electronically disrupt the desired cells into a plurality of components; and
    analyzing the components of the desired cells by hybridizing the components with probes to form probe-target hybrids within the flow cell, and detecting the probe-target hybrids while the hybrids are within the flow cell, wherein the probes are coupled to the electrodes.

12. The method of claim 11, wherein the attractive bias maintained during the isolating the desired cells step comprises a square-wall dielectric force pattern.

13. The method of claim 11, wherein the attractive bias maintained during the isolating the desired cells step comprises a checkerboard dielectric force pattern.

14. The method of claim 11, wherein the isolating the desired cells step comprises generating a dielectric force pattern having a plurality of field maxima and a plurality of field minima, wherein the attractive bias comprises the field maxima, and the undesired cells collect at the field minima.

15. The method of claim 11, wherein the creating a dielectric force pattern step comprises biasing all of the individual electrodes as a single array.

16. The method of claim 11, wherein the creating a dielectric force pattern step comprises biasing the individual electrodes as a plurality of subarrays, each subarray usable for a function chosen from the group consisting of cell separation, cell lysis, and cell analysis.

17. The method of claim 11, further comprising, after lysing the desired cells:
purifying the desired cells by introducing a protease into the flow cell via the input port, maintaining a temperature of substantially 60° C. in the flow cell to treat the desired cells with the protease, and maintaining a temperature of substantially 95° C. in the flow cell to inactivate the protease after treating the desired cells with the protease, wherein maintaining a temperature is accomplished using a heat element coupled to the flow cell and contained within the portable housing.

18. The method of claim 17, further comprising:
treating the purified desired cells with an enzyme to release a specific protein of interest from the desired cells, wherein the enzyme is introduced into the flow cell via the input port.

19. The method of claim 18, further comprising:
amplifying the specific protein of interest, and
labeling the specific protein of interest with a marker.

20. The method of claim 19, wherein the amplifying is performed by polymerase chain reaction.

21. The method of claim 19, wherein the amplifying is performed by strand displacement amplification.

22. The method of claim 11, wherein detecting the probe-target hybrids is performed using fluorophore-labeled reporter probes and an optical imaging system configured to detect the reporter probes.

23. A method for performing an analysis of a biological sample having desired cells and undesired cells using an integrated portable system, the method comprising:
providing an integrated portable system comprising an electronic system having a flow cell, a plurality of individually addressable electrodes positioned within the flow cell, a plurality of probes coupled to the electrodes, a detector configured to detect the probes, a power source coupled to the flow cell, and a portable housing containing the electronic system, the detector, and the power source;
introducing the sample into the integrated portable system by injecting the sample into the flow cell via an input port coupled to the flow cell, wherein the input port is accessed through the portable housing;
creating a dielectric force pattern by individually biasing the electrodes positioned within the flow cell;
subjecting the sample to the dielectric force pattern to separate the undesired cells from the desired cells in the sample;
isolating the desired cells by maintaining an attractive bias for the desired cells and introducing a flow of wash buffer through the flow cell via the input port to eliminate the undesired cells, wherein the undesired cells are removed from the flow cell via an output port coupled to the flow cell;
lysing the desired cells by applying an electric force within the flow cell to electronically disrupt the desired cells into a plurality of components; and
analyzing the components of the desired cells by hybridizing the components with probes to form probe-target hybrids within the flow cell, and detecting the probe-target hybrids while the hybrids are within the flow cell.

* * * * *